US012629169B2

(12) United States Patent
Madej et al.

(10) Patent No.: US 12,629,169 B2
(45) Date of Patent: May 19, 2026

(54) HIGH PRESSURE PROTECTION FOR JET ASPIRATION CATHETER

(71) Applicant: Boston Scientific Scimed, Inc., Maple Grove, MN (US)

(72) Inventors: Alyssa Madej, Minnetonka, MN (US); Michael P Schrom, Forest Lake, MN (US); Anthony Frank Tassoni, Jr., Andover, MN (US); Breanne Retherford, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 176 days.

(21) Appl. No.: 18/415,780

(22) Filed: Jan. 18, 2024

(65) Prior Publication Data

US 2024/0245422 A1      Jul. 25, 2024

Related U.S. Application Data

(60) Provisional application No. 63/440,249, filed on Jan. 20, 2023.

(51) Int. Cl.
*A61B 17/3203* (2006.01)
*A61M 25/00* (2006.01)

(52) U.S. Cl.
CPC ... *A61B 17/32037* (2013.01); *A61M 25/0023* (2013.01); *A61M 25/005* (2013.01)

(58) Field of Classification Search
CPC ..... A61B 17/32037; A61B 2090/0801; A61M 25/0023; A61M 25/005

(Continued)

(56) References Cited

U.S. PATENT DOCUMENTS 2,568,566  A      9/1951   Edward
5,370,609  A     12/1994   Drasler et al.
(Continued)

FOREIGN PATENT DOCUMENTS

EP        2362751 B1      9/2016
EP        2120737 B1      4/2020
(Continued)

OTHER PUBLICATIONS

International Search Report and Written Opinion for International Application No. PCT/US2024/011915 dated Mar. 21, 2024. (12 pages).

*Primary Examiner* — Jocelin C Tanner
(74) *Attorney, Agent, or Firm* — Seager Tufte & Wickhem, LLP

(57) ABSTRACT

Thrombectomy catheter and high-pressure protection systems for protecting a catheter shaft from high-pressure fluid jets. An illustrative thrombectomy catheter may comprise a catheter body including a catheter lumen extending therethrough. A high-pressure fluid supply tube extends through the catheter lumen from the catheter body proximal end region toward the catheter body distal end region. The high-pressure fluid supply tube is configured for communication with a fluid source near the catheter body proximal end region. The high-pressure fluid supply tube includes jet orifices for expelling fluid jets from the high-pressure fluid supply tube within the catheter lumen. Reinforcement members are disposed within the catheter lumen such that fluid jets expelled from the jet orifices impinge against the reinforcement members.

19 Claims, 11 Drawing Sheets

(58) Field of Classification Search
USPC ........................................................ 606/159
See application file for complete search history.

(56) References Cited

U.S. PATENT DOCUMENTS

| | | | |
|---|---|---|---|
| 5,425,723 A | 6/1995 | Wang | |
| 5,785,675 A | 7/1998 | Drasler et al. | |
| 5,976,103 A | 11/1999 | Martin | |
| 5,989,210 A | 11/1999 | Morris et al. | |
| 5,989,271 A | 11/1999 | Bonnette et al. | |
| 6,096,001 A | 8/2000 | Drasler et al. | |
| 6,129,697 A | 10/2000 | Drasler et al. | |
| 6,224,570 B1 | 5/2001 | Le et al. | |
| 6,258,061 B1 | 7/2001 | Drasler et al. | |
| 6,368,316 B1 * | 4/2002 | Jansen | A61M 25/005 604/525 |
| 6,471,683 B2 | 10/2002 | Drasler et al. | |
| 6,544,209 B1 | 4/2003 | Drasler et al. | |
| 6,558,366 B1 | 5/2003 | Drasler et al. | |
| 6,676,627 B1 | 1/2004 | Bonnette et al. | |
| 6,676,637 B1 | 1/2004 | Bonnette et al. | |
| 6,719,718 B2 | 4/2004 | Bonnette et al. | |
| 6,755,803 B1 | 6/2004 | Le et al. | |
| 6,764,483 B1 | 7/2004 | Bonnette et al. | |
| 6,805,684 B2 | 10/2004 | Bonnette et al. | |
| 6,875,193 B1 | 4/2005 | Bonnette et al. | |
| 6,926,726 B2 | 8/2005 | Drasler et al. | |
| 6,932,828 B2 | 8/2005 | Bonnette et al. | |
| 6,945,951 B1 | 9/2005 | Bonnette et al. | |
| 6,984,239 B1 | 1/2006 | Drasler et al. | |
| 7,220,269 B1 | 5/2007 | Ansel et al. | |
| 7,226,433 B2 | 6/2007 | Bonnette et al. | |
| 7,486,175 B2 | 2/2009 | Suzuki et al. | |
| 7,572,244 B2 | 8/2009 | Weisel et al. | |
| 7,615,031 B2 | 11/2009 | Bonnette et al. | |
| 7,842,010 B2 | 11/2010 | Bonnette et al. | |
| 7,846,175 B2 | 12/2010 | Bonnette et al. | |
| 7,879,022 B2 | 2/2011 | Bonnette et al. | |
| 7,935,077 B2 | 5/2011 | Kneip et al. | |
| 7,951,161 B2 | 5/2011 | Bonnette et al. | |
| 7,996,974 B2 | 8/2011 | Kozak et al. | |
| 8,012,117 B2 | 9/2011 | Bonnette et al. | |
| 8,162,877 B2 | 4/2012 | Bonnette et al. | |
| 8,162,878 B2 | 4/2012 | Bonnette et al. | |
| 8,303,538 B2 | 11/2012 | Bonnette et al. | |
| 8,353,858 B2 | 1/2013 | Kozak et al. | |
| 8,430,837 B2 | 4/2013 | Jenson et al. | |
| 8,439,878 B2 | 5/2013 | Bonnette et al. | |
| 8,475,487 B2 | 7/2013 | Bonnette et al. | |
| 8,491,523 B2 | 7/2013 | Scherger et al. | |
| 8,597,238 B2 | 12/2013 | Bonnette et al. | |
| 8,647,294 B2 | 2/2014 | Bonnette et al. | |
| 8,657,777 B2 | 2/2014 | Kozak et al. | |
| 8,900,179 B2 | 12/2014 | Jenson et al. | |
| 8,998,843 B2 | 4/2015 | Bonnette et al. | |
| 9,078,691 B2 | 7/2015 | Morris et al. | |
| 9,510,854 B2 | 12/2016 | Mallaby | |
| 9,662,137 B2 | 5/2017 | Jenson et al. | |
| 9,833,257 B2 | 12/2017 | Bonnette et al. | |
| 9,883,877 B2 | 2/2018 | Look et al. | |
| 10,004,846 B2 | 6/2018 | Bonnette et al. | |
| 10,314,608 B2 | 6/2019 | Jenson et al. | |
| 10,492,805 B2 | 12/2019 | Culbert et al. | |
| 10,499,944 B2 | 12/2019 | Mallaby | |
| 10,561,440 B2 | 2/2020 | Look et al. | |
| 10,716,583 B2 | 7/2020 | Look et al. | |
| 11,553,942 B2 * | 1/2023 | Bonnette | A61B 17/32037 |
| 2005/0096607 A1 | 5/2005 | Beck | |
| 2006/0106285 A1 | 5/2006 | Boulais et al. | |
| 2006/0129091 A1 | 6/2006 | Bonnette et al. | |
| 2008/0188793 A1 | 8/2008 | Kozak et al. | |
| 2008/0275383 A1 * | 11/2008 | Weisel | A61B 17/22 604/35 |
| 2008/0275393 A1 | 11/2008 | Bonnette et al. | |
| 2008/0319386 A1 | 12/2008 | Bonnette et al. | |
| 2011/0015564 A1 | 1/2011 | Bonnette et al. | |
| 2013/0046282 A1 | 2/2013 | O'Day et al. | |
| 2013/0310845 A1 | 11/2013 | Scherger, III et al. | |
| 2014/0005699 A1 | 1/2014 | Bonnette et al. | |
| 2014/0088610 A1 | 3/2014 | Bonnette et al. | |
| 2014/0214060 A1 | 7/2014 | Bonnette et al. | |
| 2014/0228869 A1 | 8/2014 | Bonnette et al. | |
| 2014/0277006 A1 | 9/2014 | Bonnette et al. | |
| 2017/0216503 A1 | 8/2017 | Look et al. | |
| 2018/0207397 A1 | 7/2018 | Look et al. | |
| 2018/0228502 A1 | 8/2018 | Shaffer et al. | |
| 2019/0209745 A1 * | 7/2019 | Hanson | A61B 17/32037 |
| 2019/0274704 A1 | 9/2019 | Jenson et al. | |
| 2020/0015840 A1 | 1/2020 | Mallaby | |
| 2020/0022711 A1 | 1/2020 | Look et al. | |
| 2020/0121356 A1 | 4/2020 | Look et al. | |
| 2020/0155178 A1 | 5/2020 | Culbert et al. | |
| 2020/0297363 A1 | 9/2020 | Look et al. | |
| 2022/0287766 A1 | 9/2022 | Richards et al. | |
| 2022/0370084 A1 | 11/2022 | Quillin | |

FOREIGN PATENT DOCUMENTS

| | | |
|---|---|---|
| EP | 3689274 A1 | 8/2020 |
| EP | 3145557 B1 | 1/2021 |
| EP | 3821921 A1 | 5/2021 |
| EP | 3570901 B1 | 5/2022 |
| JP | 5385155 B2 | 1/2014 |
| WO | 0151116 A2 | 7/2001 |
| WO | 2008097339 A2 | 8/2008 |
| WO | 2017041062 A1 | 3/2017 |
| WO | 2017177022 A1 | 10/2017 |
| WO | 2019140132 A1 | 7/2019 |

* cited by examiner

HIGH PRESSURE PROTECTION FOR JET ASPIRATION CATHETER

CROSS-REFERENCE TO RELATED APPLICATIONS

This application claims the benefit of U.S. Provisional Patent Application Ser. No. 63/440,249, filed Jan. 20, 2023, which is incorporated herein by reference.

TECHNICAL FIELD

The disclosure is directed to thrombectomy systems. More particularly, the disclosure is directed to a reinforced catheter shaft for withstanding localized high-pressure fluid jets.

BACKGROUND

Thrombectomy is a procedure for removing thrombus from the vasculature of a patient. Mechanical and fluid-based systems can be used to remove thrombus. With fluid-based systems, an infusion fluid may be infused to a treatment area of a vessel with a catheter to dislodge the thrombus. In some instances, an effluent (e.g., the infusion fluid and/or blood) including the dislodged thrombus may be extracted from the vessel through the catheter. Of the known thrombectomy systems and methods, there is an ongoing need to provide alternative configurations of thrombectomy catheters and systems, as well as methods of operating such thrombectomy systems.

SUMMARY

This disclosure provides design, material, manufacturing method, and use alternatives for medical devices.

In a first example, a thrombectomy catheter may comprise a catheter body extending from a proximal end region to a distal end region and including a catheter lumen extending between the proximal end region and the distal end region, a high-pressure fluid supply tube extending through the catheter lumen from the catheter body proximal end region toward the catheter body distal end region, the high-pressure fluid supply tube configured for communication with a fluid source near the catheter body proximal end region, at least one jet orifice for expelling at least one fluid jet from said high-pressure fluid supply tube within the catheter lumen, an entrainment inflow orifice positioned along the catheter distal portion, and at least one reinforcement member disposed within the catheter lumen. The at least one fluid jet expelled from the at least one jet orifice may impinge against the at least one reinforcement member.

Alternatively or additionally to any of the examples above, in another example, the at least one reinforcement member may comprise a generally tubular body including a plurality of slots extending through a sidewall of the generally tubular body.

Alternatively or additionally to any of the examples above, in another example, the plurality of slots may each have a length that extends circumferentially about the generally tubular body.

Alternatively or additionally to any of the examples above, in another example, the plurality of slots may be longitudinally spaced about a length of the generally tubular body.

Alternatively or additionally to any of the examples above, in another example, the generally tubular body may include at least one region free from the plurality of slots.

Alternatively or additionally to any of the examples above, in another example, the at least one region free from the plurality of slots may be positioned adjacent to the at least one jet orifice for impingement of the at least one fluid jet there against.

Alternatively or additionally to any of the examples above, in another example, the at least one reinforcement member may comprise a braided tubular body.

Alternatively or additionally to any of the examples above, in another example, the braided tubular body may include regions of a lower pic count alternating with regions of a higher pic count along a length of the braided tubular body.

Alternatively or additionally to any of the examples above, in another example, the at least one reinforcement member may comprise a tubular collar and a wing portion extending longitudinally from the collar.

Alternatively or additionally to any of the examples above, in another example, the wing portion may be configured to extend less than 270° about an inner circumference of the catheter body.

Alternatively or additionally to any of the examples above, in another example, the at least one reinforcement member may be secured to the catheter body.

Alternatively or additionally to any of the examples above, in another example, the at least one reinforcement member may be secured to the high-pressure fluid supply tube.

Alternatively or additionally to any of the examples above, in another example, the at least one reinforcement member may comprise a plurality of reinforcement members axially spaced along a length of the high-pressure fluid supply tube.

Alternatively or additionally to any of the examples above, in another example, the at least one reinforcement member may extend from a proximal end of the high-pressure fluid supply tube to a distal end of the high-pressure fluid supply tube.

Alternatively or additionally to any of the examples above, in another example, the at least one reinforcement member may comprise polyimide, polyether-ether-ketone (PEEK), stainless steel, or nitinol.

In another example, a thrombectomy catheter may comprise a catheter body extending from a proximal end region to a distal end region and including a catheter lumen extending between the proximal end region and the distal end region, a high-pressure fluid supply tube extending through the catheter lumen from the catheter body proximal end region toward the catheter body distal end region, the high-pressure fluid supply tube configured for communication with a fluid source near the catheter body proximal end region, a plurality of jet orifices for expelling a plurality of fluid jets from said high-pressure fluid supply tube within the catheter lumen, the plurality of jet orifices spaced along a length of the high-pressure fluid supply tube, an entrainment inflow orifice positioned along the catheter distal portion and a plurality of reinforcement members disposed within the catheter lumen, the plurality of reinforcement members spaced along a length of the catheter lumen and each reinforcement member positioned adjacent to a jet orifice. Each reinforcement member of the plurality of reinforcement members may comprise an impingement location for impingement of one of the plurality of fluid jet thereagainst.

Alternatively or additionally to any of the examples above, in another example, the plurality of reinforcement members may be regions of a tubular member devoid of slots, and the tubular member includes regions having a plurality of slots extending through a sidewall of the tubular member between adjacent ones of the regions devoid of slots.

Alternatively or additionally to any of the examples above, in another example, the plurality of reinforcement members may be regions of a braided tubular member having a higher pic count, and the braided tubular member includes regions having a lower pic count between adjacent ones of the regions having a higher pic count.

In another example, a thrombectomy catheter may comprise a catheter body extending from a proximal end region to a distal end region and including a catheter lumen extending between the proximal end region and the distal end region, a high-pressure fluid supply tube extending through the catheter lumen from the catheter body proximal end region toward the catheter body distal end region, the high-pressure fluid supply tube configured for communication with a fluid source near the catheter body proximal end region, a plurality of jet orifices for expelling a plurality of fluid jets from said high-pressure fluid supply tube within the catheter lumen, the plurality of jet orifices spaced along a length of the high-pressure fluid supply tube, an entrainment inflow orifice positioned along the catheter distal portion, and a reinforcement member disposed within the catheter lumen, the reinforcement member extending along a length of the high-pressure fluid supply tube and comprising a generally tubular body including a plurality of slots extending through a sidewall of the generally tubular body and a plurality of regions free from slots.

Alternatively or additionally to any of the examples above, in another example, the plurality of regions free from slots may be generally aligned with an impingement location of the plurality of fluid jets.

The above summary of some example embodiments is not intended to describe each disclosed embodiment or every implementation of the disclosure.

BRIEF DESCRIPTION OF THE DRAWINGS

The disclosure may be more completely understood in consideration of the following detailed description of various embodiments in connection with the accompanying drawings, in which.

Figure 1:
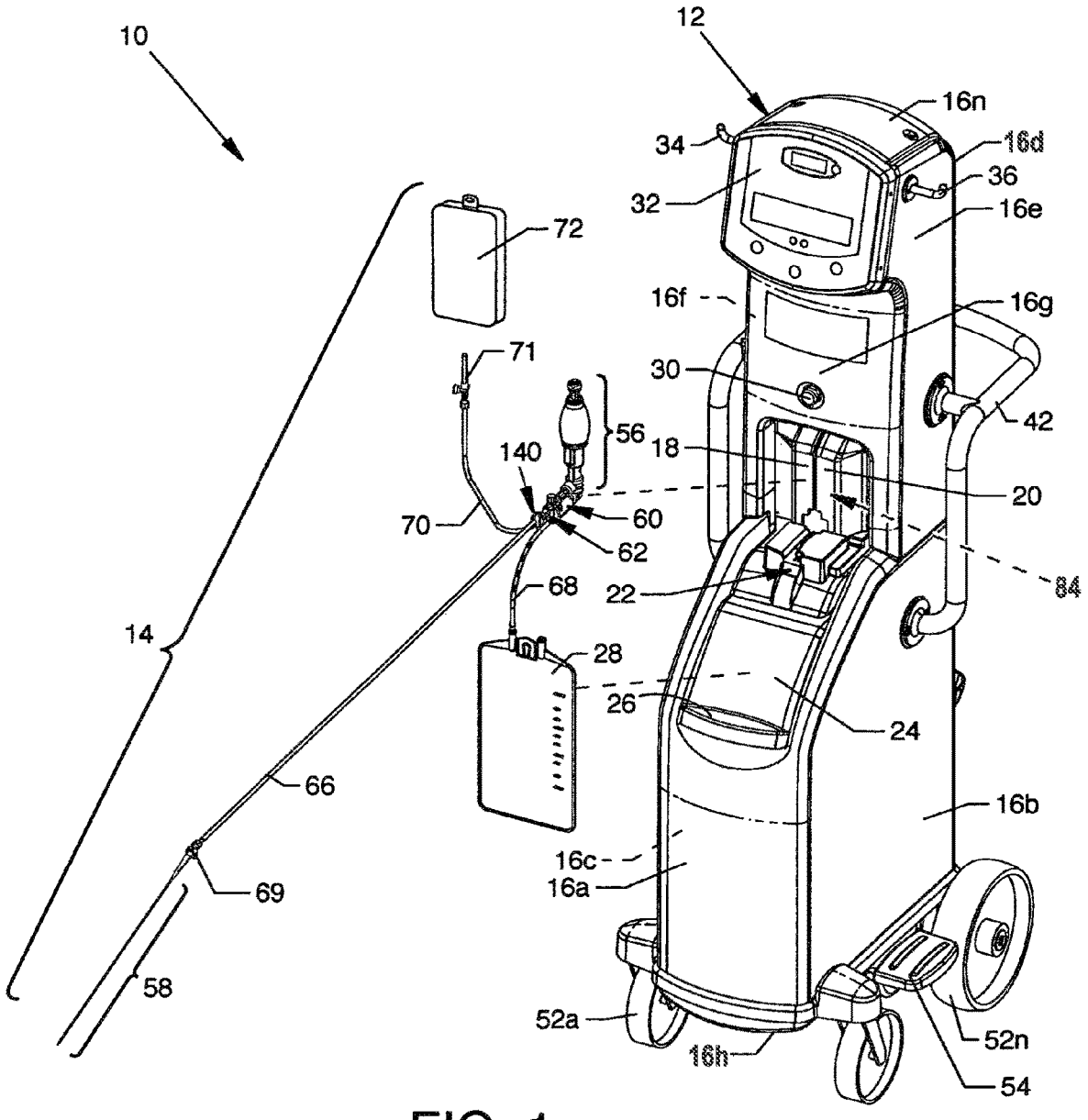
FIG. 1 is a perspective view of an illustrative thrombectomy system.

While the disclosure is amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

All numeric values are herein assumed to be modified by the term "about", whether or not explicitly indicated. The term "about" generally refers to a range of numbers that one of skill in the art would consider equivalent to the recited value (e.g., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Thrombectomy catheters and systems may be used to remove thrombus, plaques, lesions, clots, etc. from veins or arteries. Some thrombectomy catheter may use a jet tube that curves in a way that the jets point directly backward into the catheter (e.g., parallel to the shaft walls) to prevent shaft damage. However, this curved jet tube design may block a significant portion of the cross-sectional area of the aspiration lumen, which may in turn, decrease aspiration rates. Further this type of jet orientation may require a side port which may limit the vessel diameter that the device is able to reach as well as increasing the presence of hemolysis in the target vessels. Other jet aspiration catheters may utilize high velocity saline jets in a series to entrain fluid or clot material into and through the shaft of the catheter. To obtain high performance, the velocity of the jets, and therefore localized pressures, are extremely high. Most thin walled polymer shafts cannot withstand these pressures without additional support. Disclosed herein are a variety of catheter shaft designs or reinforcements that allow the catheter assembly to withstand localized high pressures created by the saline jets, while also maintaining the necessary flexibility in the areas where pressures are lower.

FIG. 1 is a perspective view of an illustrative thrombectomy system 10. The thrombectomy system 10 may include a control console or drive unit 12 and a pump/catheter assembly 14. In some instances, the pump/catheter assembly 14 may be a single use device in which a new pump/catheter assembly 14 may be used with the drive unit 12 for each medical procedure. Shown on the drive unit 12 are a plurality of removable panels 16a-16n about and along the drive unit 12 enclosing the internal structure of the drive unit 12. An illustrative drive unit 12 is described in commonly assigned U.S. Pat. No. 7,935,077, titled THROMBECTOMY CATHETER DEPLOYMENT SYSTEM, the disclosure of which is hereby incorporated by reference. Centrally located in the drive unit 12 and aligned to the lower region of the panel 16g may be automatically opening doors 18 and 20 which open to expose the interior of the drive unit 12 to provide access to a carriage assembly 22. The carriage assembly 22, which may accommodate components of the pump/catheter assembly 14, as discussed further herein, is shown accessible via opening the closed doors 18 and 20. The drive unit 12 may include a catch basin for collecting fluid leakage from the components of the pump/catheter assembly 14. For example, a removable drip tray 24 is shown located on the front of the drive unit 12 extending from below the carriage assembly 22 toward the panel 16a. Other configurations of catch basins are also contemplated. The drip tray 24 and a removable receptacle 26 may collectively support and accommodate an effluent collection bag, such as effluent collection bag 28 of the pump/catheter assembly 14. In other instances, the drive unit 12 may include a different structure, such as a hook for hanging the effluent collection bag 28 from, or a shelf for setting the effluent collection bag 28 on. In instances where the carriage assembly 22 is movable, a carriage assembly activation switch 30 may be provided with the drive unit 12, such as located on panel 16g, to selectively position the carriage assembly 22 inwardly or outwardly. A user interface 32, including memory capabilities, may be provided with the drive unit 12, such as located at the upper region of the drive unit 12 between the upper regions of the upper side panels 16e and 16f. Saline bag hooks 34 and 36 may extend through the panels 16e and 16f to hang saline bags therefrom. The drive unit 12 may include a handle 42 as well as a plurality of wheels 52a-52n and brake pedals 54 for wheel lockage to assist in maneuvering the drive unit 12 by medical personnel.

The pump/catheter assembly 14, which may be a disposable single-use device, is shown unattached from the drive unit 12. The pump/catheter assembly 14 includes a pump 56 and a thrombectomy catheter 58. During use, a portion of the pump/catheter assembly 14 may be secured within a portion of the drive unit 12. Other components included in the pump/catheter assembly 14 may include a bubble trap 60 attached to the pump 56, a connection manifold assembly 62 connected to the bubble trap 60, an effluent return tube 66 connected between the connection manifold assembly 62 and the thrombectomy catheter 58, a high-pressure fluid supply tube 64 attached between the output of the pump 56 and the thrombectomy catheter 58 which may be coaxially arranged inside the effluent return tube 66, a transition fixture 69 between the distal end of the effluent return tube 66 and the proximal end of the thrombectomy catheter 58, an effluent waste tube 68 connecting the effluent collection bag 28 to the connection manifold assembly 62, and a fluid supply tube 70 having a bag spike 71 connecting a fluid supply bag 72 (e.g., a saline bag) to the connection manifold assembly 62. The fluid supply tube 70 may be in fluid communication with the interior of the bubble trap 60 to provide fluid from the fluid supply bag 72 to the pump 56 and then to the thrombectomy catheter 58 through the high-pressure fluid supply tube 64.

Figure 2:
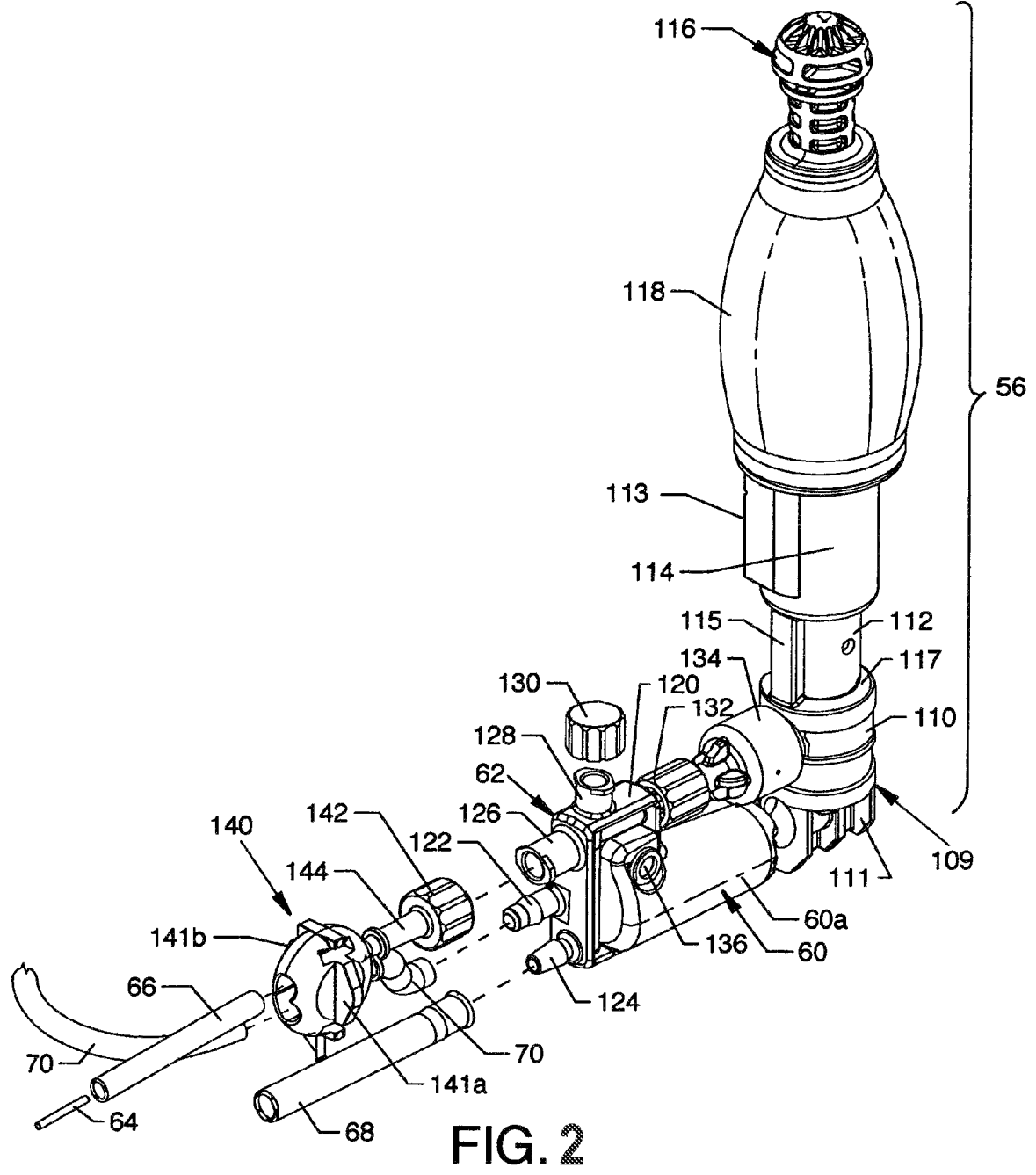
FIG. 2 is a partially exploded perspective view of the pump, the bubble trap, the connection manifold assembly, and an associated fixture of the pump/catheter assembly for use in the thrombectomy system of FIG. 1.

FIG. 2 is a partially exploded perspective view of several components of the pump/catheter assembly 14 generally including the pump 56, the bubble trap 60, the connection manifold assembly 62, and a fixture 140. The pump 56 centers about a tubular body 112. Components are located about the lower region of the tubular body 112 and include a base 109 having an upper portion 110 and a lower portion 111 both positioned about the lower region of the tubular body 112. An annular surface 117 is included at the top of the upper portion 110 of the base 109 for intimate contact with capture tabs of the carriage assembly 22 to contain the pump 56 within the carriage assembly 22. A top body 114, is positioned about the upper region of the tubular body 112. The base 109 and the top body 114, as well as a connecting panel 115, may be molded or otherwise suitably constructed to encompass the greater part of the tubular body 112, for example. A data plate 113 may also be included on the top body 114 for the inclusion of a barcode, an RFID tag, or other informational displays to determine operational parameters of the device.

Figure 3:
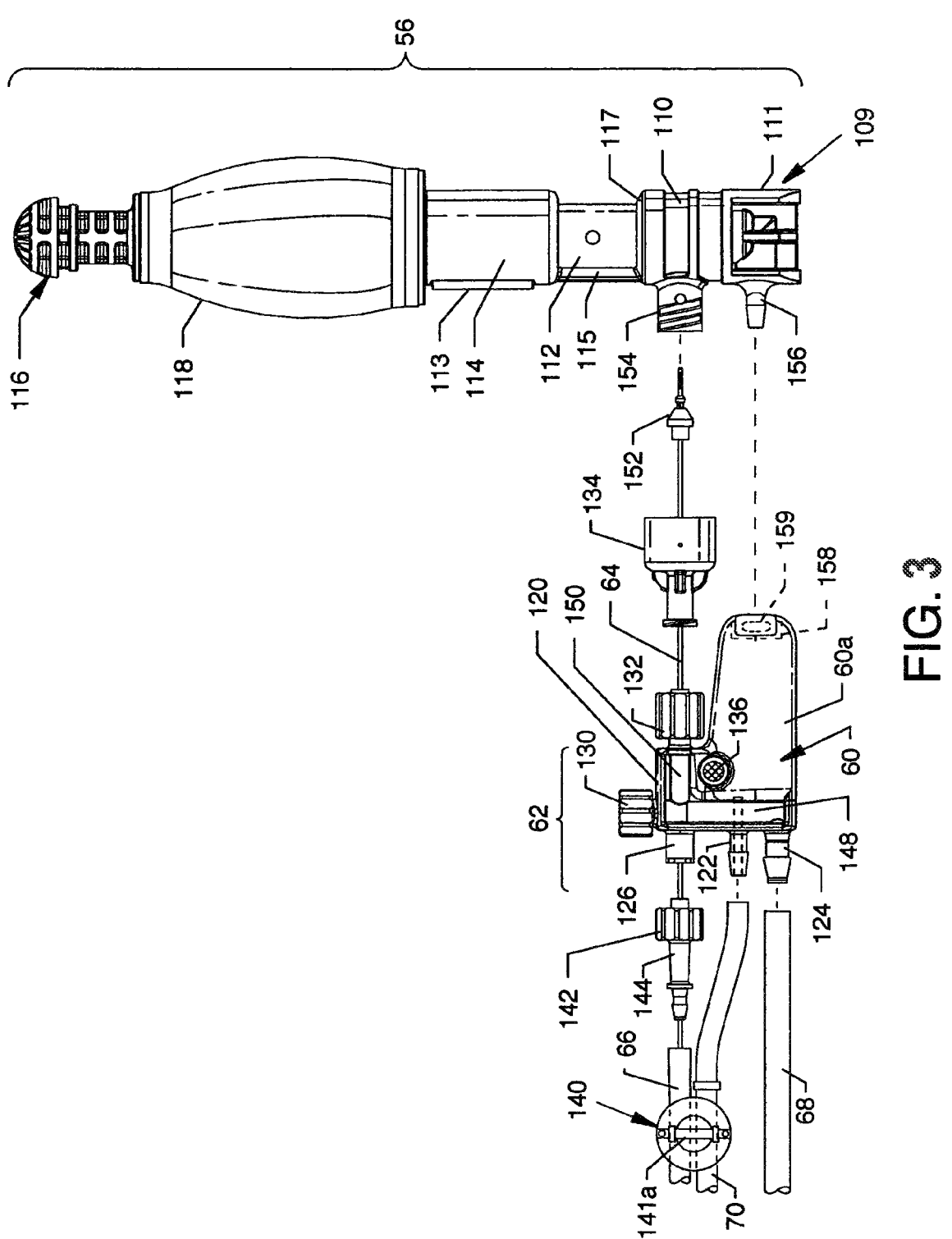
FIG. 3 is a partially exploded side view of the pump, the bubble trap, the connection manifold assembly, and associated fixture of the pump/catheter assembly for use in the thrombectomy system of FIG. 1.

The pump 56 may include a hemispherically-shaped pump piston head 116 having a flexible boot 118 connected to and extending between the top body 114 and the pump piston head 116. In some instances, the geometrically configured lower portion 111 of the base 109 may serve as a mount for one end of the bubble trap 60 (FIG. 3).

The connection manifold assembly 62 may be secured directly to the other end of the bubble trap 60 and in some instances may include a bracket 120 to which is attached a vertically oriented tubular manifold 148 having a plurality of ports attached or formed therethrough including a fluid (e.g., saline) inlet port 122, an effluent outlet port 124, a Luer style effluent return port 126, and/or an auxiliary port 128 and cap 130. Also shown are connectors 132 and 134 connectingly extending between the connection manifold assembly 62 and the upper portion 110 of the base 109.

The bubble trap 60 may include mating halves of which one mating half 60a is shown. A hydrophobic filter 136 may be included at the upper forward region of the bubble trap half 60a. Another hydrophobic filter may be included on the second bubble trap half (not explicitly shown) which opposes the hydrophobic filter 136 on the bubble trap half 60a.

The fixture 140, and components associated therewith, assists in support and connection of the effluent return tube 66 to the effluent return port 126 by a connector 142 combined continuously with a connection tube 144, and also assists in support, passage and connection of the fluid supply tube 70 with the fluid inlet port 122. The fixture 140 may include outwardly extending vertically aligned and opposed tabs 141a and 141b which prevent the fixture 140 and associated effluent return tube 66 containing the high-pressure fluid supply tube 64 and the fluid supply tube 70 from contacting a roller pump (not explicitly shown) provided with the drive unit 12, such as located in the carriage assembly 22 or adjacent thereto.

FIG. 3 is a partially exploded side view of the elements of FIG. 2 illustrating the relationship of the pump 56, the bubble trap 60, the connection manifold assembly 62, and the fixture 140. Also shown is the vertically oriented tubular manifold 148 secured to the bracket 120. The effluent outlet port 124 may be connected to and in fluid communication with the lower interior of the tubular manifold 148. The effluent return port 126 may be connected to and in fluid communication with the upper interior of the tubular manifold 148. Also connecting to the tubular manifold 148 is a horizontally aligned passage port 150 and associated connector 132, each opposing the effluent return port 126. The passage port 150 may accommodate the high-pressure fluid supply tube 64 which extends distally through the lumen (not explicitly shown) of the passage port 150, the connector 132, the upper region of the tubular manifold 148, the effluent return port 126, the connector 142, the connection tube 144, and into and through the effluent return tube 66 in coaxial fashion to connect to the thrombectomy catheter 58 (FIG. 1). The proximal end of the high-pressure fluid supply tube 64 includes a high-pressure fitting 152 located near the proximal end of the high-pressure fluid supply tube 64 to facilitate connection of the high-pressure fluid supply tube 64 in fluid communication with the interior of the pump 56. The proximal end of the high-pressure fluid supply tube 64, which is the inlet to the high-pressure fluid supply tube 64, may include a plurality of very small holes (not shown) comprising a filter at the proximal end thereof. The connector 134, which may have internal and/or external threads, may be aligned over and about the high-pressure fluid supply tube 64 distal to the high-pressure fitting 152 and threadingly engage a threaded connection port 154 extending horizontally from the upper portion 110 of the base 109 of the pump 56. The connector 134 may be rotated to threadably engage the high-pressure fitting 152 with corresponding mating threaded structure provided with the pump 56. A connector 132 may be utilized to engage the externally threaded end of the connector 134 to secure the connector 134, and thus the pump 56, to the connection manifold assembly 62 and to provide for fixation of the bubble trap 60 to the pump 56. In addition, direct connection and fluid communication between the pump 56 and the bubble trap 60 may be provided by a horizontally oriented pump fluid inlet port 156 which engages a corresponding receptor port 158 and seal 159 interior to one end of the bubble trap 60. The fluid inlet port 122 located on the bracket 120 may extend behind the tubular manifold 148 to communicate with the interior of the bubble trap 60 for fluid (e.g., saline) debubbling, whereby unpressurized fluid (e.g., saline) is made available for use by the pump 56.

Figure 4:
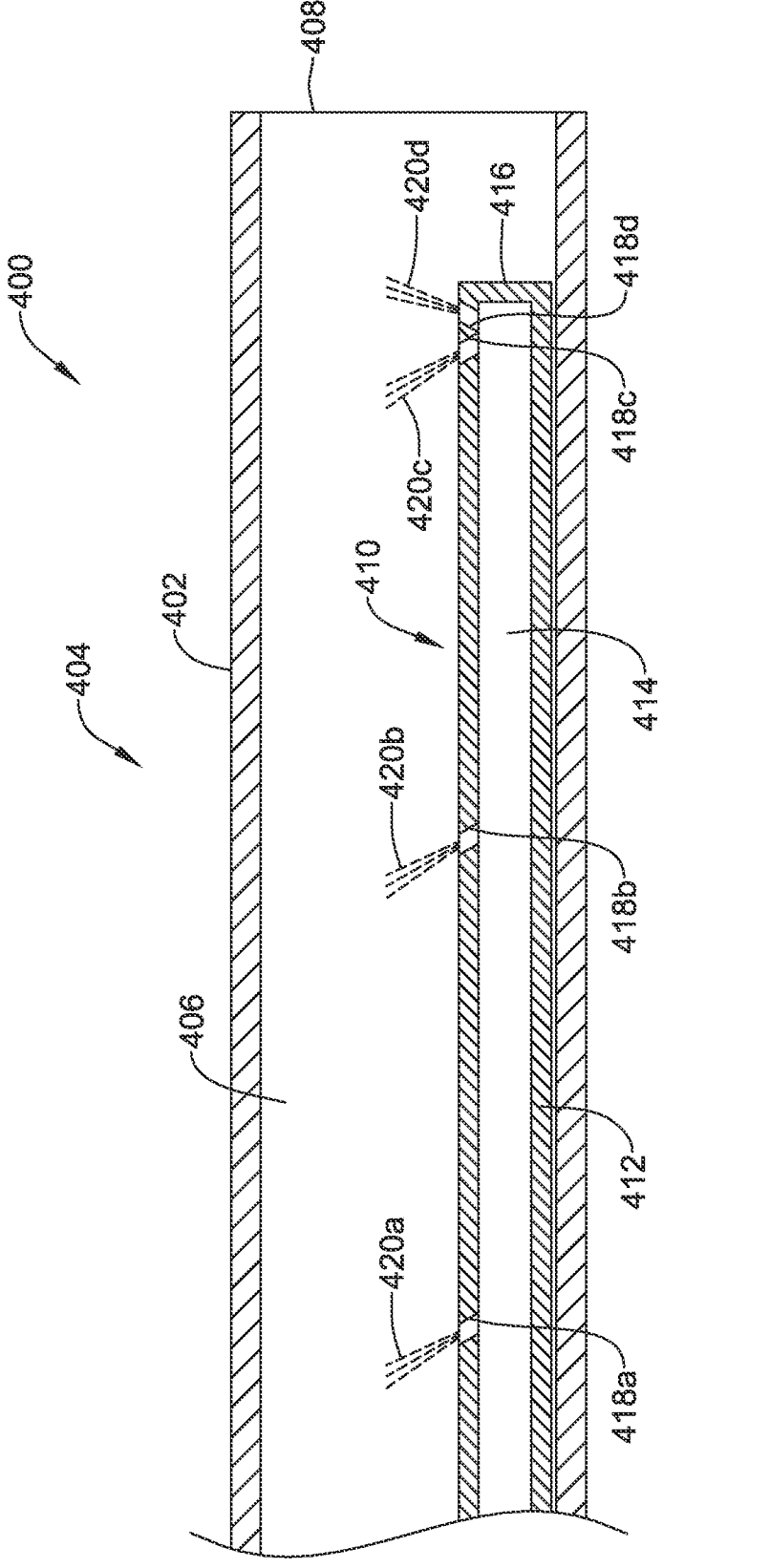
FIG. 4 is a longitudinal cross-sectional view of a distal end region of an illustrative thrombectomy catheter.

FIG. 4 is a cross-sectional view of a distal end region 404 of an illustrative thrombectomy catheter 400. The thrombectomy catheter 400 may be one illustrative example of the thrombectomy catheter 58 described above. The thrombectomy catheter 400 may include a tubular member or catheter body 402 extending from a proximal end region (not explicitly shown) configured to remain outside the body to a distal end region 404. The catheter body 402 may be one illustrative example of the effluent return tube 66 of the thrombectomy catheter 58 described above. A lumen 406 may extend from the proximal end region to the distal end region 404 of the catheter body 402. The catheter body 402 may terminate at a distally facing distal opening 408 at the distal end of the catheter body 402. In some instances, the distal opening 408 may be in a plane that extends generally orthogonal to a longitudinal axis of the catheter body 402. In other instances, the distal opening 408 may be in a plane that extends generally oblique to a longitudinal axis of the catheter body 402. Generally, the distal opening 408 may be an entrainment inflow orifice. While not explicitly shown, the catheter body 402 may include one or more markers (e.g., radiopaque marker bands) disposed along the catheter body 402. Further, while not explicitly shown, in some embodiments, the catheter body 402 may include one or more openings extending through a side wall thereof, if desired.

The thrombectomy catheter 400 may further include a high-pressure fluid supply tube 410. The high-pressure fluid supply tube 410 may be one illustrative example of the high-pressure fluid supply tube 66 of the thrombectomy catheter 58 described above. The high-pressure fluid supply tube 410 may be disposed within the lumen 406 of the catheter body 402. The high-pressure fluid supply tube 410 may include a supply tube wall 412 defining a lumen or fluid pathway 414 extending therethrough. In at least some instances, the high-pressure fluid supply tube 410 may have a closed distal end 416. Because of this, fluid may be able to pass through the fluid pathway 414 but does not exit the distal end. The high-pressure fluid supply tube 410 may extend along a length of the catheter body 402 with the distal end 416 located within the lumen 406 of the catheter body 402 proximal to the distal opening 408 at the distal end of the catheter body 402. A proximal end of the high-pressure fluid supply tube 410 may be in fluid communication with the pump 56 described herein, to provide high-pressure fluid to the fluid pathway 414 of the high-pressure fluid supply tube 410.

A plurality of jet orifices 418*a-d* (collectively, 418) may be defined along the supply tube wall 412. For example, the supply tube wall 412 may include two, three, four, five, six, or more jet orifices 418. The jet orifices 418 may be spaced along the supply tube wall 412 at any desired intervals. For example, each of the jet orifices 418 may be equidistantly spaced from adjacent jet orifices 418 along the length of the supply tube wall 412. In other instances, the jet orifices 418 may be arranged such that the spacing between adjacent jet orifices 418 near the distal end of the supply tube wall 412 is closer than the spacing between adjacent jet orifices 418 near the proximal end of the supply tube wall 412. For instance, the spacing between the orifices 418 may gradually increase as you move proximally along the length of the shaft, or the spacing may increase in a step-wise configuration. In some instances, some or all of the jet orifices 418 may be axially aligned along the supply tube wall 412. In other instances, one or more of the jet orifices 418 may be circumferentially offset from one another about the supply tube wall 412. A number of patterns are contemplated including a helical pattern, a pattern where no two jet orifices 418 are disposed at the same axial location, a regular pattern including two or more jet orifices 418 disposed at the same axial location, an irregular pattern (where some of the jet orifices 418 may or may not be disposed at the same axial location), etc. The jet orifices 418 may be formed using a suitable method such as electron discharge machining, etching, cutting (e.g., including laser cutting), or the like. In some instances, one or more of the jet orifices 418 may have a substantially round shape. In other instances, one or more of the jet orifices 418 may have a substantially non-round shape (e.g., oval, polygonal, irregular, etc.). In some instances, the jet orifices 418 may be beveled or otherwise include a beveled surface.

At least some of the jet orifices 418*a-c* may be designed to infuse fluid (e.g., a motive fluid, a liquid, a gas or air, steam, a fluid with particles disposed therein, or the like) through the jet orifices 418*a-c* and into the lumen 406 of the catheter body 402 in a generally proximal direction as depicted by lines 420*a-c* representing motive jetted fluid projecting generally proximally from the jet orifices 418*a-c*. For example, each of the jet orifices 418*a-c* may be arranged at an acute angle to the longitudinal axis of the supply tube wall 412 such that the jet orifices 418*a-c* angle in a proximal direction. In some embodiments, one or more of the jet orifices 418*d* may be designed to infuse fluid (e.g., a motive fluid, a liquid, a gas or air, steam, a fluid with particles disposed therein, or the like) through the jet orifice(s) 418*d* and into the lumen 406 of the catheter body 402 in a generally distal direction as depicted by lines 420*d* representing motive jetted fluid projecting generally distally from the jet orifice 418*d*. For example, the jet orifice 418*d* may be arranged at an oblique angle to the longitudinal axis of the supply tube wall 412 such that the jet orifice 418*d* angles in a distal direction. The distally projecting jet orifice 418*d* may be the distalmost jet orifice, with the proximally projecting jet orifices 418*a-c* positioned proximal of the distally projecting jet orifice 418*d*. The distally projecting jet orifice 418*d* may break up particles as they are drawn into the lumen 406 of the catheter body 402 while the proximally projecting jet orifices 418*a-c* may move particles proximally along the catheter body 402.

In some instances, the jet orifices 418 may be oriented at an angle relative to the longitudinal axis of the supply tube wall 412. For example, the proximally oriented jet orifices 418*a-c* may be oriented at an oblique (e.g., acute) angle relative to the longitudinal axis of the supply tube wall 412 and/or oriented at an angle greater than zero degrees and less than ninety degrees relative to the longitudinal axis of the supply tube wall 412. It is contemplated that a distally oriented jet orifice 418*d* may be oriented at an oblique (e.g., obtuse) angle relative to the longitudinal axis of the supply tube wall 412 and/or oriented at an angle greater than 90 degrees and less than 180 degrees relative to the longitudinal axis of the supply tube wall 412. In other instances, the jet orifices 418 may be oriented perpendicular to the longitudinal axis of the supply tube wall 412 (e.g., at an angle of about 90 degrees relative to the longitudinal axis of the supply tube wall 412). The angle may or may not be the same for all the jet orifice 418. Infusion of motive fluid through the lumen 414 of the supply tube wall 412 may result in fluid being jetted through the jet orifices 418 (e.g., generally in the proximal direction) and the generation of an aspiration force.

In at least some instances, the jet orifices 418 may be understood as being arranged in series. In other words, the jet orifices 418 may be arranged at various locations along the longitudinal axis of the supply tube wall 412. For example, the jet orifices 418 may be uniformly or non-uniformly spaced along of a length of the supply tube wall 412. This may position the jet orifices 418 at axially spaced apart locations within the catheter body 402 and along the length thereof. For example, the jet orifices 418 may be spaced along an entire length of the supply tube wall 412 and correspondingly along an entire length of the catheter body 402, or portions thereof, as desired. In some examples, the jet orifices 418 may be spaced at intervals in the range of every 5 inches (12.7 centimeters (cm)) to every 15 inches (38.1 cm), or in the range of every 6 inches (15.2 cm) to every 12 inches (30.5 cm) along a length of the supply tube wall 412. In other instances, the spacing between the jet orifices 418 may be less than every 5 inches (12.7 cm) or greater than every 15 inches (38.1 cm). Accordingly, motive fluid leaves via the jet orifices 418 forming a jetted motive fluid 420*a-d* (collectively, 420). The jetted motive fluid 420 may reach speeds of 17,150 centimeters/second or greater (e.g., half the speed of sound, or greater). This jetted motive fluid 420 enters an entrainment material where the shear layer between the two causes turbulence, mixing, and transfer of momentum. Entrainment material may enter the distal opening 408 and then may be urged proximally by momentum transfer. As the mixture of jetted motive fluid 420 and entrainment material migrates proximally, the material may sequentially approach a number of jet orifices 418. Upon interaction with the jetted motive fluid 420 from each individual jet orifice 418, the momentum in the entrainment material mixture may increase, and the thrombogenic material may more readily flow proximally through the catheter body 402 for removal. The increase in momentum may allow for the catheter body 402 to be used without a second or outflow orifice (e.g., positioned proximally of the distal opening 408). Alternatively, some of the entrapped thrombogenic material may exit the catheter body 402 through a second orifice (not shown) positioned proximal to the distal opening 408, recirculate to the distal opening 408 (e.g., one or more times), and then move through the lumen 406 of the catheter body 402.

The performance of the thrombectomy catheter 400 and the high-pressure fluid supply tube 410 may be directly related to the velocity of the motive fluid 420 exiting the jet orifices 418 and the localized pressure created by the jetted motive fluid 420. For example, the more powerful the jetted motive fluid 420, the higher the aspiration rates may be. It is further contemplated that increasing the velocity may allow the thrombectomy catheter 400 to be used to break up and remove acute, sub-acute, and/or chronic clots. However, increasing the jet power may damage a standard polymer inner liner of the catheter body 402 which may not be robust enough to withstand the localized pressures directed radially across the inner diameter of the catheter body 402. It is contemplated that the catheter body 402 may benefit from regions configured to withstand the high-pressure impact of the jetted motive fluid 420 impinging on the inner wall of the catheter body 402 while maintaining the overall flexibility of the catheter body 402 required to navigate tortuous anatomy.

Figures 5A, 5B:
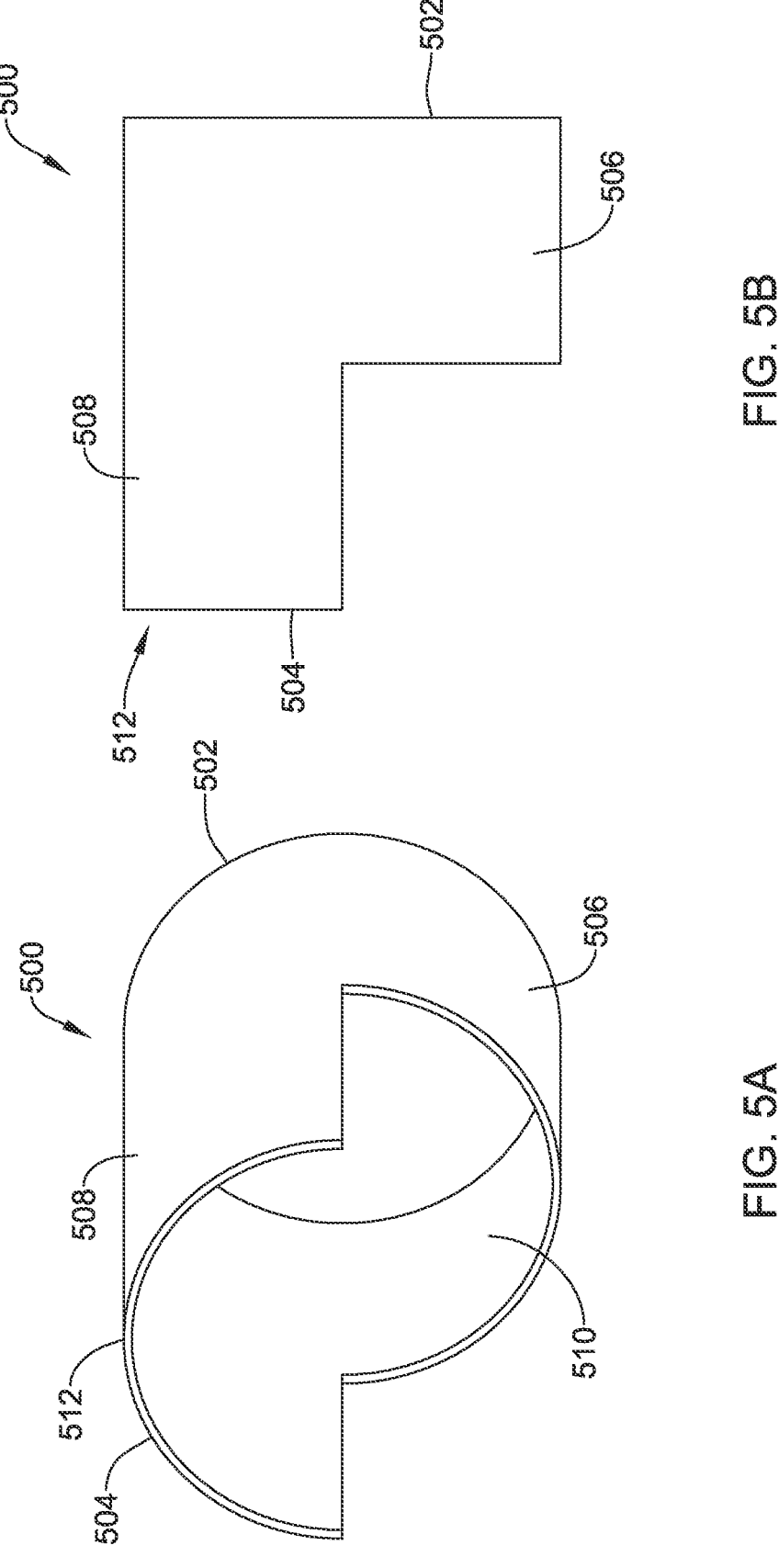
FIG. 5A is a perspective view of an illustrative reinforcement member.
FIG. 5B is a side view of the illustrative reinforcement member of FIG. 5A.

FIG. 5A is a perspective view of an illustrative reinforcement member 500 that may be used protect the inner diameter of the catheter body 402 at points of high-pressure impingement by the jetted motive fluid 420. FIG. 5B is a side view of the illustrative reinforcement member 500 of FIG. 5A. A plurality of reinforcement members 500 may be spaced along a length of the thrombectomy catheter 400 such that the high-pressure jetted motive fluid 420 impinges the reinforcement members 500 rather than directly impacting the inner surface of the catheter body 402. For example, a reinforcement member 500 may be positioned at or adjacent to the impingement location of each jet orifice 418. The impingement location may be axially offset from the jet orifice 418 or at a longitudinally similar location. In some cases, a single member 500 may cover the impingement location of more than one jet orifice 418. In other cases, a reinforcement member 500 may cover the impingement location of a single jet orifice 418, such that a separate reinforcement member 500 is associated with each jet orifice 418. In some embodiments, the reinforcement member 500 may be affixed or secured to the catheter body 402 and in other embodiments, the reinforcement member 500 may be affixed or secured to the high-pressure fluid supply tube 410, as will be described in more detail herein. The reinforcement member 500 may be formed from a high modulus material that has a high resistance to shear, such as, but not limited to, polyimides, polyether-ether-ketone (PEEK), other high-performance plastics, stainless steel, nitinol, other metals, etc. It is contemplated that the material of the reinforcement member 500 may be selected to withstand the high-pressure impingement of the jetted motive fluid 420. In some examples, the reinforcement member 500 may be heat treated to improve the flexibility of the reinforcement member 500. Alternatively, or additionally, portions of the reinforcement member 500 may include laser-cut slots to increase flexibility.

The reinforcement member 500 may extend from a first end 502 to a second end 504. The reinforcement member 500 may have an outer diameter or outer cross-sectional dimension that is similar to the inner diameter of the catheter body 402. The reinforcement member 500 may include a generally tubular collar 506 adjacent the first end 502 and a longitudinally extending wing portion 508 extending longitudinally from the tubular collar 506 to the second end 504. The tubular collar 506 and the wing portion 508 may be formed as a single monolithic structure or may be formed as separate components that are subsequently coupled together. The tubular collar 506 may define a lumen 510 extending therethrough. The wing portion 508 may have a generally semi-cylindrical shape having a convex outer surface configured to conform to an inner surface of the catheter body 402 and an opposite concave surface for impingement of the high-pressure jetted motive fluid 420 thereagainst. The wing portion 508 may be configured to extend less than 360° about an inner circumference of the catheter body 402. In some cases, the wing portion 508 may be configured extend 270° or less, 180° or less, 90° or less, etc. about the inner circumference of the catheter body 402. In other examples, the wing portion 508 may extend 360° about an inner circumference of the catheter body 402 such that the entire reinforcement member 500 is a generally tubular member. It is contemplated that the arc length of the wing portion 508 and/or a length thereof may be determined, at least in part, by an angle of the jet orifices 418 and/or an area of impingement of the jetted motive fluid 420. For example, a jet orifice 418 having an angle closer to 90° may impinge a smaller area of the inner wall of the catheter body 402 than a jet orifice having an angle closer to 0° or 180° relative to a longitudinal axis of the high-pressure fluid supply tube 410. Thus, the closer the angle of the jet orifice 418 is to 90° the smaller (e.g., arc length and/or length) the wing portion 508 of the reinforcement member 500 may be. It is further contemplated that a length of the wing portion 508 may take into account variability in the jet orifice 418 location and/or bends in the catheter body 402. It is contemplated that the wing portion 508 may take other shapes, as desired. While FIGS. 5A and 5B illustrate the wing portion 508 as having a generally planar end 512, in some cases, the end of the wing portion 508 may be curved, oblong (almond-like shape), or other regular or irregular shapes to reduce an amount of material present. In some examples, the first and/or second ends 502, 504 of the reinforcement member 500 may include tapered or beveled edges. For example, it may be desirable for the reinforcement member 500 to minimize features which increase friction and/or turbulence.

Figure 5C:
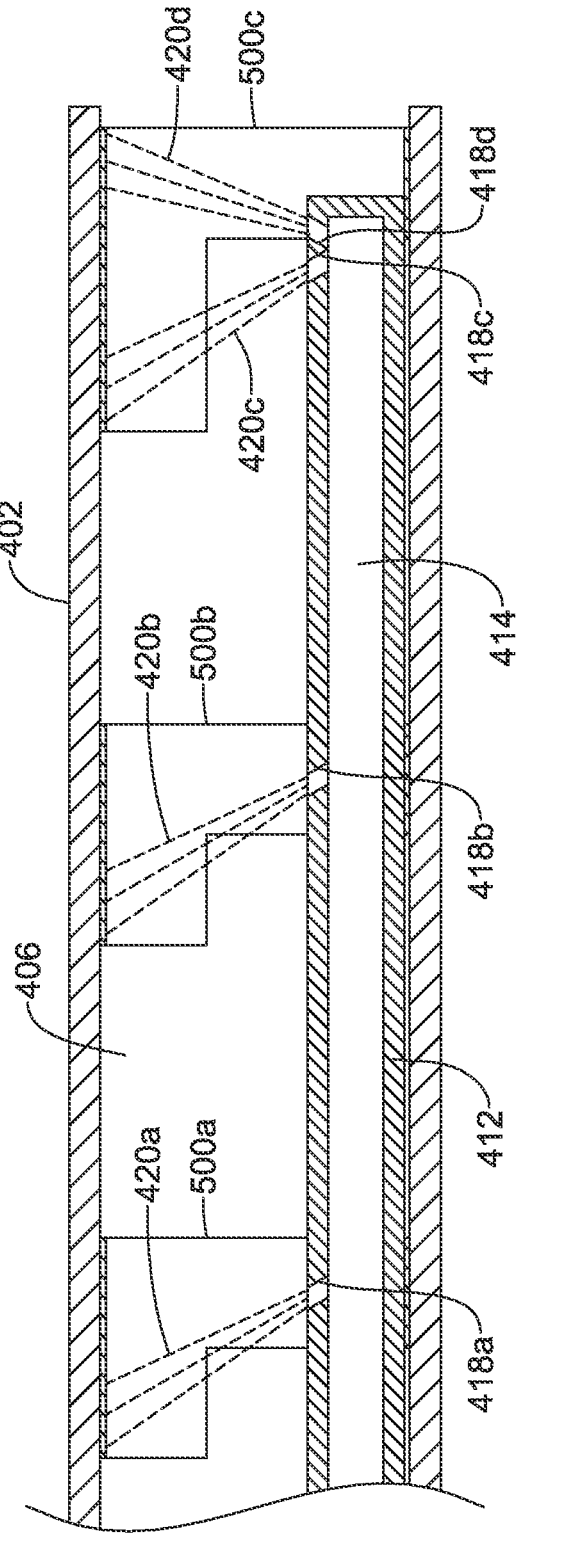
FIG. 5C is a longitudinal cross-sectional view of the distal end region of an illustrative thrombectomy catheter including a plurality of reinforcement members.

FIG. 5C is a cross-sectional view of the distal end region 404 of the illustrative thrombectomy catheter 400 including a plurality of reinforcement members 500a-c (collectively, 500) arranged within the lumen 406 of the catheter body 402. While FIG. 5C illustrates only the distal end region 404 of the thrombectomy catheter 400, it should be understood that the reinforcement members 500 may be positioned anywhere from the proximal end to the distal end of the thrombectomy catheter 400. In some examples, the distalmost reinforcement member 500c may be aligned or positioned to protect the impingement locations of both a proximally facing jet orifice 418c and a distally facing jet orifice 418d. For example, the distalmost reinforcement member 500c may extend distally beyond the distal end 416 of the supply tube wall 412. However, this is not required. In some embodiments, a separate reinforcement member 500 may be used to provide impingement protection for each of the proximally facing jet orifices 418c and the distally facing jet orifice 418d individually. In some embodiments, the reinforcement members 500 may be secured to or otherwise incorporated with the catheter body 402 by positioning the reinforcement members 500 on a mandrel and reflowing or otherwise forming the catheter body 402 over the reinforcement members 500. Alternatively, or additionally, the reinforcement members 500 may be secured directly to the high-pressure fluid supply tube 410. For example, the reinforcement members 500 may be welded, glued, adhered, crimped, etc. directly onto the high-pressure fluid supply tube 410 adjacent to the jet orifices 418. The high-pressure fluid supply tube 410 and reinforcement member 500 assembly may then be inserted into the lumen 406 of the catheter body 402.

It is contemplated that during assembly, the reinforcement members 500 may be oriented to provide impingement protection based on the orientation of the jetted orifice 418 and the jetted motive fluid 420. For example, the wing portion 508 may be positioned to extend proximally from the collar 506 when the reinforcement member 500 is positioned adjacent to a proximally oriented jet orifice 418a-c while the wing portion 508 may be positioned to extend distally from the collar 506 when the reinforcement member 500 is positioned adjacent to a distally oriented jet orifice 418d. As can be seen in FIG. 5C, regions of the catheter body 402 where the jetted motive fluid 420 does not impact the inner surface of the catheter body 402 may be free from a reinforcement member 500. This may help maintain the flexibility of the catheter body 402 while also precluding or limiting damage to the catheter body 402 that may be caused by the high-pressure impingement of the jetted motive fluid 420. In some examples, the reinforcement members 500 may be axially offset from the respective jet orifice 418. In other examples, the reinforcement members 500 may be at an axially similar location as the respective jet orifice 418. The axial length of the wing portion 508 may be sufficient to span the length of impingement of the high-pressure jetted motive fluid 420 on the catheter body 402.

In some embodiments, one or more reinforcement members 500 may be provided in areas or regions free from high-pressure impingement of the jetted motive fluid 420. For example, if a thrombectomy catheter 400 requires greater pushability in the proximal region, a section of one or more reinforcement members 500 can be added in that region of the thrombectomy catheter 400 to improve pushability by adding stiffness.

Figures 6A, 6B:
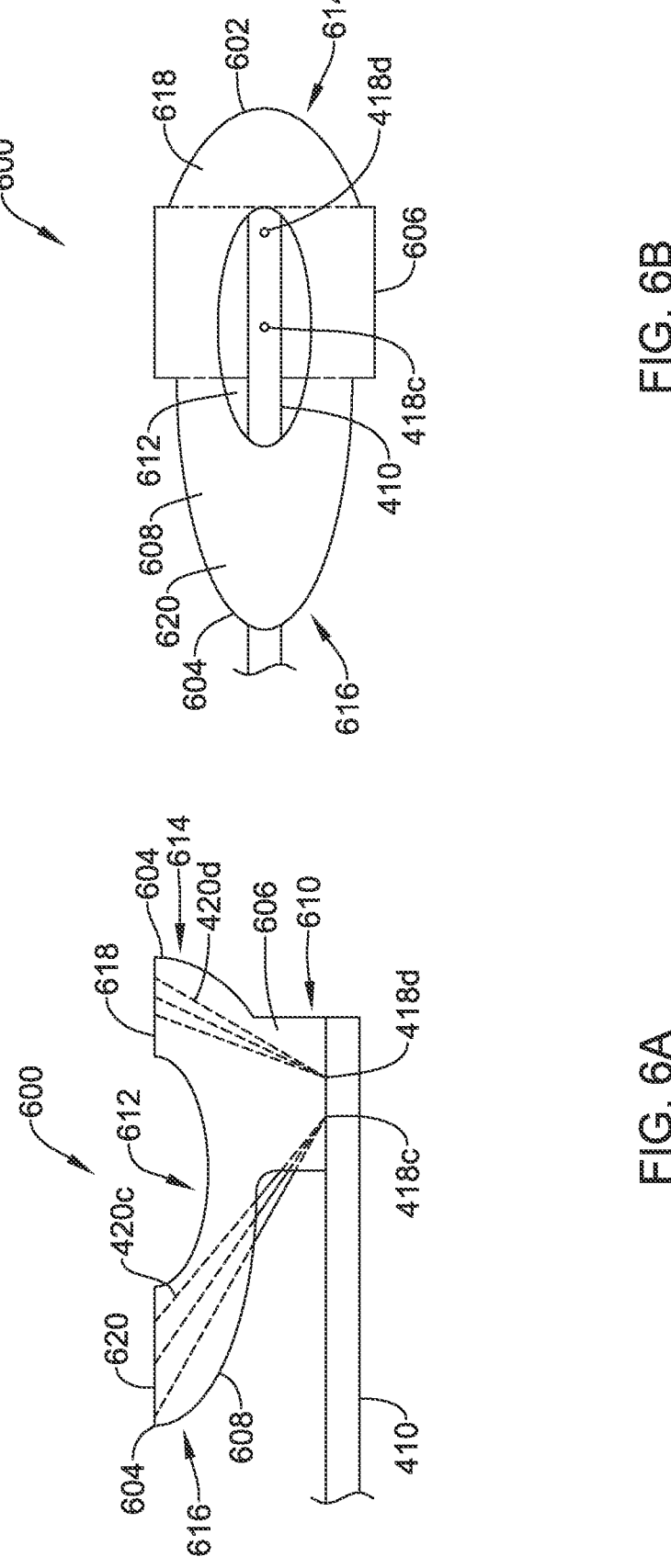
FIG. 6A is a side view of another illustrative reinforcement member.
FIG. 6B is a top view of the illustrative reinforcement member of FIG. 6A.

FIG. 6A is a side view of another illustrative reinforcement member 600 with the high-pressure fluid supply tube 410 that may be used to protect the inner diameter (i.e., luminal surface) of the catheter body 402 (not explicitly shown in FIGS. 6A and 6B) at points of high-pressure impingement. FIG. 6B is a top view of the illustrative reinforcement member 600 of FIG. 6A. A plurality of reinforcement members 600 may be spaced along a length of the thrombectomy catheter 400 such that the high-pressure jetted motive fluid 420 impinges the reinforcement member 600 rather than directly impacting the inner surface of the catheter body 402 in a manner similar to that illustrated in FIG. 5C. For example, a reinforcement member 600 may be positioned adjacent to the impingement location of each jet orifice 418. In some cases, a single member 600 may cover the impingement location of more than one jet orifice 418. In some embodiments, the reinforcement member 600 may be affixed or secured to the catheter body 402 and in other embodiments, the reinforcement member 600 may be affixed or secured to the high-pressure fluid supply tube 410. The reinforcement member 600 may be formed from a high modulus material that has a high resistance to shear, such as, but not limited to, polyimides, polyether-ether-ketone (PEEK), other high-performance plastics, stainless steel, nitinol, other metals, etc. It is contemplated that the material of the reinforcement member 600 may be selected to withstand the high-pressure impingement of the jetted motive fluid 420. In some examples, the reinforcement member 600 may be heat treated to improve flexibility. Alternatively, or additionally, portions of the reinforcement member 600 may include laser-cut slots to increase flexibility.

The reinforcement member 600 may extend from a first end 602 to a second end 604. The reinforcement member 600 may have an outer diameter or outer cross-sectional dimension that is similar to the inner diameter of the catheter body 402. The reinforcement member 600 may include a generally tubular collar 606 adjacent the first end 602 and a longitudinally extending wing portion 608 extending from tubular collar 606 and between the first end 602 and the second end 604. The wing portion 608 may include a first end region 618 and a second end region 620. The tubular collar 606 may define a lumen 610 extending therethrough. In some examples, the tubular collar 606 may be discontinuous about a circumference thereof. For example, the tubular collar 606 and/or the wing portion 608 may include an opening or aperture 612 extending through a wall thickness thereof. The aperture 612 may be sized and shaped such that motive jetted fluid 420 impinges an inner surface of the wing portion 608. However, the removal of material to form the aperture 612 may increase the flexibility of the reinforcement member 600. This may help the reinforcement member 600 to provide the desired high-pressure protection while minimizing the impact of the reinforcement member 600 on the overall flexibility of the thrombectomy catheter 400.

The wing portion 608 may have a generally curved shape having a convex outer surface configured to conform to an inner surface of the catheter body 402 and an opposite concave surface for impingement of the high-pressure jetted motive fluid 420 thereagainst. In some examples, the ends 614, 616 of the wing portion 608 may be curved or rounded (e.g., have an almond-like shape). In other examples, the ends 614, 616 of the wing portion 608 may take other regular or irregular shapes, as desired. In some examples, the first and/or second ends 602, 604 of the reinforcement member 600 may include tapered or beveled edges. For example, it may be desirable for the reinforcement member 600 to minimize features which increase friction and/or turbulence. The wing portion 608 may be configured to extend less than 360° about an inner circumference of the catheter body 402. In other examples, the wing portion 608 may extend 360° about an inner circumference of the catheter body 402 such that the reinforcement member 600 is a generally tubular member. In some cases, the wing portion 608 may be configured extend 270° or less, 180° or less, 90° or less, etc.

about the inner circumference of the catheter body 402. It is contemplated that the arc length of the wing portion 608 and/or a length thereof may be determined, at least in part, by an angle of the jet orifices 418 and/or an area of impingement of the jetted motive fluid 420. For example, a jet orifice 418 having an angle closer to 90° may impinge a smaller area of the inner wall of the catheter body 402 than a jet orifice having an angle closer to 0° or 180° relative to a longitudinal axis of the high-pressure fluid supply tube 410. Thus, the closer the angle of the jet orifice 418 is to 90° the smaller (e.g., arc length and/or length) the wing portion 608 of the reinforcement member 600 may be. It is further contemplated that a length of the wing portion 608 may take into account variability in the jet orifice 418 location and/or bends in the catheter body 402.

While FIG. 6A illustrates a single reinforcement member 600, it should be understood that any number of reinforcement members 600 may be positioned anywhere from the proximal end to the distal end of the thrombectomy catheter 400. In some examples, the wing portion 608 may be sized, shaped, and/or positioned to protect the catheter body 402 from the impingement locations of both a proximally facing jet orifice 418*c* and a distally facing jet orifice 418*d*. For example, in the illustrated embodiment, the first end region 618 of the reinforcement member 600 may be configured to provide impingement protection for a distally oriented jet orifice 418*d* while the second end region 620 of the reinforcement member 600 may be configured to provide impingement protection for a proximally oriented jet orifice 418*c*. However, this is not required. In some embodiments, a separate reinforcement member 600 may be used to provide impingement protection for each of the proximally facing jet orifice 418*c* and the distally facing jet orifice 418*d*. It is contemplated that the shape of the wing portion 608 may be sized and/or shaped based on the desired impingement protection desired. For example, when the reinforcement member 600 is providing impingement protection for only a single jet orifice 418, the wing portion 608 may be smaller than the wing portion 608 of a reinforcement member 600 providing impingement protection for two or more jet orifices 418. It is contemplated that the first end region 618 of the wing portion 608 may be omitted for a reinforcement member 600 providing impingement protection for only a single jet orifice 418. Alternatively, the second end region 620 of the wing portion 608 may be omitted for a reinforcement member 600 providing impingement protection for only a single jet orifice 418.

In some embodiments, the reinforcement members 600 may be secured to or otherwise incorporated with the catheter body 402 by positioning the reinforcement members 600 on a mandrel and reflowing or otherwise forming the catheter body 402 over the reinforcement members 600. Alternatively, or additionally, the reinforcement members 600 may be secured directly to the high-pressure fluid supply tube 410. For example, the reinforcement members 600 may be welded, glued, adhered, crimped, etc. directly onto the high-pressure fluid supply tube 410 adjacent to the jet orifices 418. The high-pressure fluid supply tube 410 and reinforcement member 600 assembly may then be inserted into the lumen 406 of the catheter body 402.

It is contemplated that during assembly, the reinforcement members 600 may be oriented to provide impingement protection based on the orientation of the jetted orifice 418 and the jetted motive fluid 420. For example, the second end region 620 of the wing portion 608 may be positioned to extend proximally from the collar 606 when the reinforcement member 600 is positioned adjacent to a proximally oriented jet orifice 418*c*. In other examples, the first end region 618 of the wing portion 608 may be positioned to extend proximally from the collar 606 when the reinforcement member 600 is positioned adjacent to a proximally oriented jet orifice 418*c*. It is further contemplated that the second end region 620 of the wing portion 608 may be positioned to extend distally from the collar 606 when the reinforcement member 600 is positioned adjacent to a distally oriented jet orifice 418*d*. Alternatively, the first end region 618 of the of the wing portion 608 may be positioned to extend distally from the collar 606 when the reinforcement member 600 is positioned adjacent to a distally oriented jet orifice 418*d*. In some examples, the reinforcement members 600 may be axially offset from the respective jet orifice 418. In other examples, the reinforcement members 600 may be at an axially similar location as the respective jet orifice 418.

While not explicitly shown, regions of the catheter body 402 where the jetted motive fluid 420 does not impact the inner surface of the catheter body 402 may be free from a reinforcement member 600. This may help maintain the flexibility of the catheter body 402 while also precluding or limiting damage to the catheter body 402 that may be caused by the high-pressure impingement of the jetted motive fluid 420. In some embodiments, one or more reinforcement members 600 may be provided in areas or regions free from pressure impingement of the jetted motive fluid 420. For example, if a thrombectomy catheter 400 requires greater pushability in the proximal region, a section of one or more reinforcement members 600 can be added in that region of the thrombectomy catheter 400 to improve pushability by adding stiffness.

Figure 7:
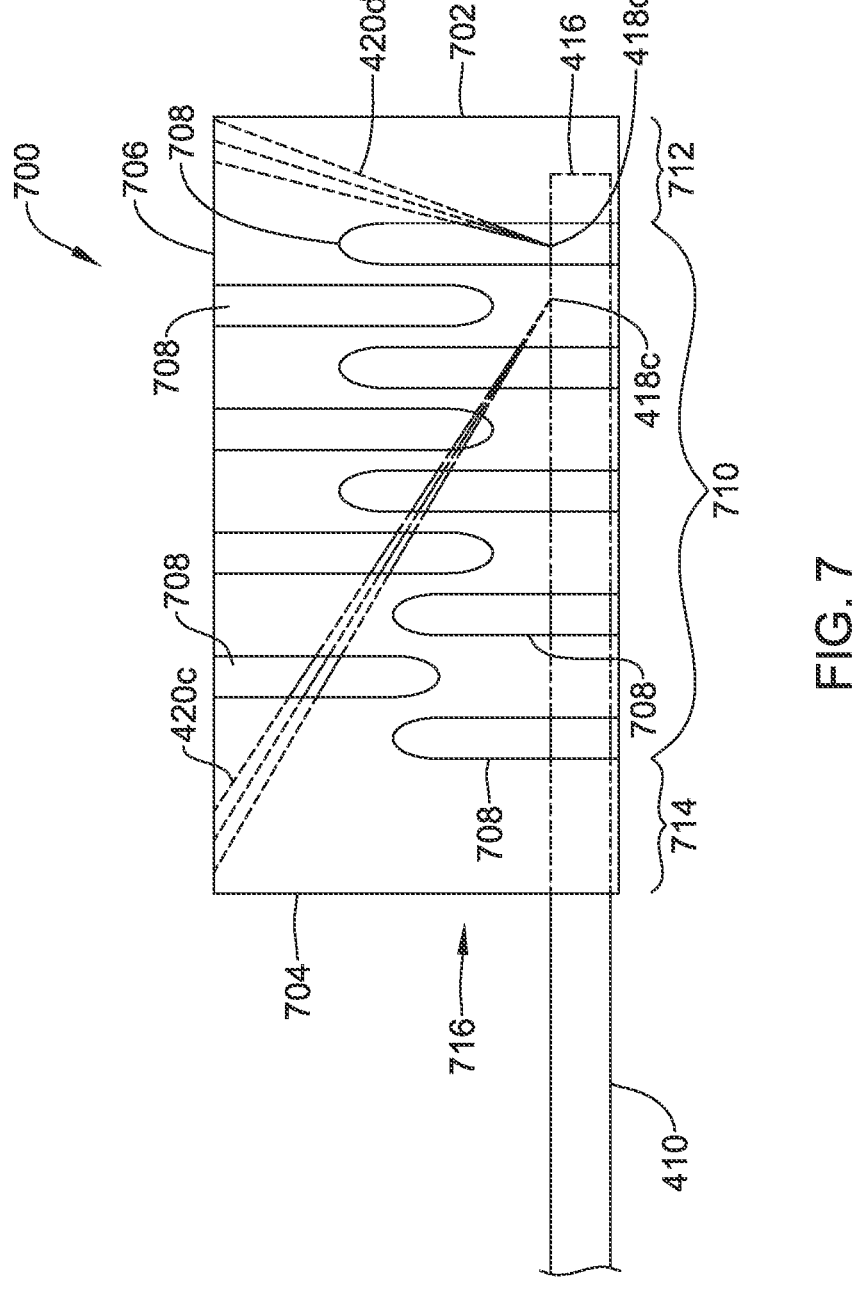
FIG. 7 is a side view of another illustrative reinforcement member.

FIG. 7 is a side view of another illustrative reinforcement member 700 with the high-pressure fluid supply tube 410 that may be used to protect the inner diameter (i.e., luminal surface) of the catheter body 402 (not explicitly shown in FIG. 7) at points of high-pressure impingement. A plurality of reinforcement members 700 may be spaced along a length of the thrombectomy catheter 400 such that the high-pressure jetted motive fluid 420 impinges the reinforcement member 700 rather than directly impacting the inner surface of the catheter body 402 in a manner similar to that illustrated in FIG. 5C. For example, a reinforcement member 700 may be positioned adjacent to the impingement location of each jet orifice 418. In some cases, a single member 700 may cover the impingement location of more than one jet orifice 418. In some embodiments, the reinforcement member 700 may be affixed or secured to the catheter body 402 and in other embodiments, the reinforcement member 700 may be affixed or secured to the high-pressure fluid supply tube 410. The reinforcement member 700 may be formed from a high modulus material that has a high resistance to shear, such as, but not limited to, polyimides, polyether-ether-ketone (PEEK), other high-performance plastics, stainless steel, nitinol, other metals, etc. It is contemplated that the material of the reinforcement member 700 may be selected to withstand the high-pressure impingement of the jetted motive fluid 420. In some examples, the reinforcement member 700 may be heat treated to improve flexibility.

The reinforcement member 700 may have a generally tubular body 706 extending from a first end 702 to a second end 704. The tubular body 706 may define a lumen 716 extending from the first end 702 to a second end 704. The outer diameter of the tubular body 706 may be similar to an inner diameter of the catheter body 402. The reinforcement member 700 may include a plurality of slots 708 cut or otherwise formed into a sidewall of the tubular body 706.

The plurality of slots 708 may be formed in any suitable manner. For example, in some embodiments, the slots 708 are formed via laser cutting. In other instances, the slots 708 may be formed by saw cutting, abrasion, or any other known cutting or grinding mechanism. The slots 708 can be dimensioned and/or located to provide a desired level of flexibility. In some examples, the slots 708 have a length that extends circumferentially about the tubular body 706. The slots 708 can be circumferentially and/or longitudinally arranged to provide the desired flexibility. In some instances, the slots 708 may extend helically about the tubular body 706. In some examples, more than one slot 708 may be present a similar longitudinal location. In some instances, the slots 708 may be equally spaced along a length of an intermediate region 710 of the tubular body 706. In other cases, the slots 708 may be, for example, more closely spaced together near the first end 702 for additional flexibility and more spaced apart near the second end 704 for additional strength, although this is not required. In other cases, the slots 708 may be more closely spaced together near the second end 704 and more spaced apart near the first end 702. In an illustrative but non-limiting embodiment, the slots 708 may have a width that is in the range of about 0.0005 inches (0.0127 millimeters (mm)) to about 0.020 inches (0.508 mm). Each slot 708 may extend about ten percent, about twenty percent, about thirty percent, about forty percent, about fifty percent, about sixty percent, about seventy percent, about eighty percent, about ninety percent or more about the circumference of the tubular body 706.

A first end region 712 and/or a second end region 714 of the tubular body 706 may be free from slots 708 to provide impingement protection for impingement of the high-pressure jetted motive fluid 420 thereagainst. For example, the slotted intermediate region 710 of the tubular body 706 may provide flexibility to the reinforcement member 700 while the generally solid first end region 712 and second end region 714, which are devoid of the slots, may allow the jetted motive fluid 420 to impact an inner surface of the reinforcement member 700 instead of an inner surface of the catheter body 402. While FIG. 7 illustrates an entirety of the circumference of the first and second end regions 712, 714 as free from slots 708, this is not required. In some examples, slots 708 may be provided in the wall of the tubular body 706 generally opposite from the area of impingement. For example, as the jetted motive fluid 420 is not expected to impinge an entire inner circumference of the catheter body 402, the entire circumference of the first and/or second end regions 712, 714 need not be free from slots 708. The length of the first end region 712 and/or the second end region 714 may be determined, at least in part, by an angle of the jet orifices 418 and/or an area of impingement of the jetted motive fluid 420. For example, a jet orifice 418 having an angle closer to 90° may impinge a smaller area of the inner wall of the catheter body 402 than a jet orifice having an angle closer to 0° or 180° relative to a longitudinal axis of the high-pressure fluid supply tube 410. Thus, the closer the angle of the jet orifice 418 is to 90° the smaller (e.g., arc length and/or length) the first end region 712 and/or a second end region 714 of the reinforcement member 700 may be. For example, in the illustrated embodiment, the angle of the distal jet orifice 418*d* is closer to 90° than the proximal jet orifice 418*c* and thus the first end region 712 may have a length that is less than a length of the second end region 714. However, this is not required. The first end region 712 and/or a second end region 714 may have similar lengths. Alternatively, the first end region 712 may have a length that is greater that length of the second end region 714. It is further contemplated that a length of the first end region 712 and/or a second end region 714 may take into account variability in the jet orifice 418 location and/or bends in the catheter body 402.

While FIG. 7 illustrates a single reinforcement member 700, it should be understood that any number of reinforcement members 700 may be positioned anywhere from the proximal end to the distal end of the thrombectomy catheter 400. In some examples, the generally solid regions or regions that are free from the plurality of slots (e.g., the first end region 712 and/or a second end region 714) may be sized, shaped, and/or positioned to protect the catheter body 402 from the impingement locations of both a proximally facing jet orifice 418*c* and a distally facing jet orifice 418*d*. For example, in the illustrated embodiment, the first end region 712 of the reinforcement member 700 may be configured to provide impingement protection for a distally oriented jet orifice 418*d* while the second end region 714 of the reinforcement member 700 may be configured to provide impingement protection for a proximally oriented jet orifice 418*c*. It is contemplated that the reinforcement member 700 may extend distally beyond the distal end 416 of the supply tube wall 412 to provide impingement protection for the distally oriented jet orifice 418*d*. However, this is not required. In some embodiments, a separate reinforcement member 700 may be used to provide impingement protection for each of the proximally facing jet orifice 418*c* and the distally facing jet orifice 418*d*. It is contemplated that the positioning of the plurality of slots 708 may be arranged based on the desired impingement protection desired. Said differently, regions of the tubular body 706 that are free from the plurality of slots 708 may be selected based on the desired impingement protection desired. For example, when the reinforcement member 700 is providing impingement protection for only a single jet orifice 418, only one of the first end region 712 or the second end region 714 may be free from the plurality of slots 708. This may provide the desired impingement protection while maintaining the flexibly of the thrombectomy catheter 400.

In some embodiments, the reinforcement members 700 may be secured to or otherwise incorporated with the catheter body 402 by positioning the reinforcement members 700 on a mandrel and reflowing or otherwise forming the catheter body 402 over the reinforcement members 700. Alternatively, or additionally, the reinforcement members 700 may be secured directly to the high-pressure fluid supply tube 410. For example, the reinforcement members 700 may be welded, glued, adhered, crimped, etc. directly onto the high-pressure fluid supply tube 410 adjacent to the jet orifices 418. The high-pressure fluid supply tube 410 and reinforcement member 700 assembly may then be inserted into the lumen 406 of the catheter body 402.

It is contemplated that during assembly, the reinforcement members 700 may be oriented to provide impingement protection based on the orientation of the jetted orifice 418 and the jetted motive fluid 420. For example, the first end region 712 and/or the second end region 714 may be oriented to provide the desired protection depending on the orientation of the adjacent jet orifice 418. In some examples, the reinforcement members 700 may be axially offset from the respective jet orifice 418. In other examples, the reinforcement members 700 may be at an axially similar location as the respective jet orifice 418.

While not explicitly shown, regions of the catheter body 402 where the jetted motive fluid 420 does not impact the inner surface of the catheter body 402 may be free from a reinforcement member 700. This may help maintain the flexibility of the catheter body 402 while also precluding or limiting damage to the catheter body 402 that may be caused by the high-pressure impingement of the jetted motive fluid 420. In some embodiments, one or more reinforcement members 700 may be provided in areas or regions free from pressure impingement of the jetted motive fluid 420. For example, if a thrombectomy catheter 400 requires greater pushability in the proximal region, a section of one or more reinforcement members 700 can be added in that region of the thrombectomy catheter 400 to improve pushability by adding stiffness.

Figure 8:
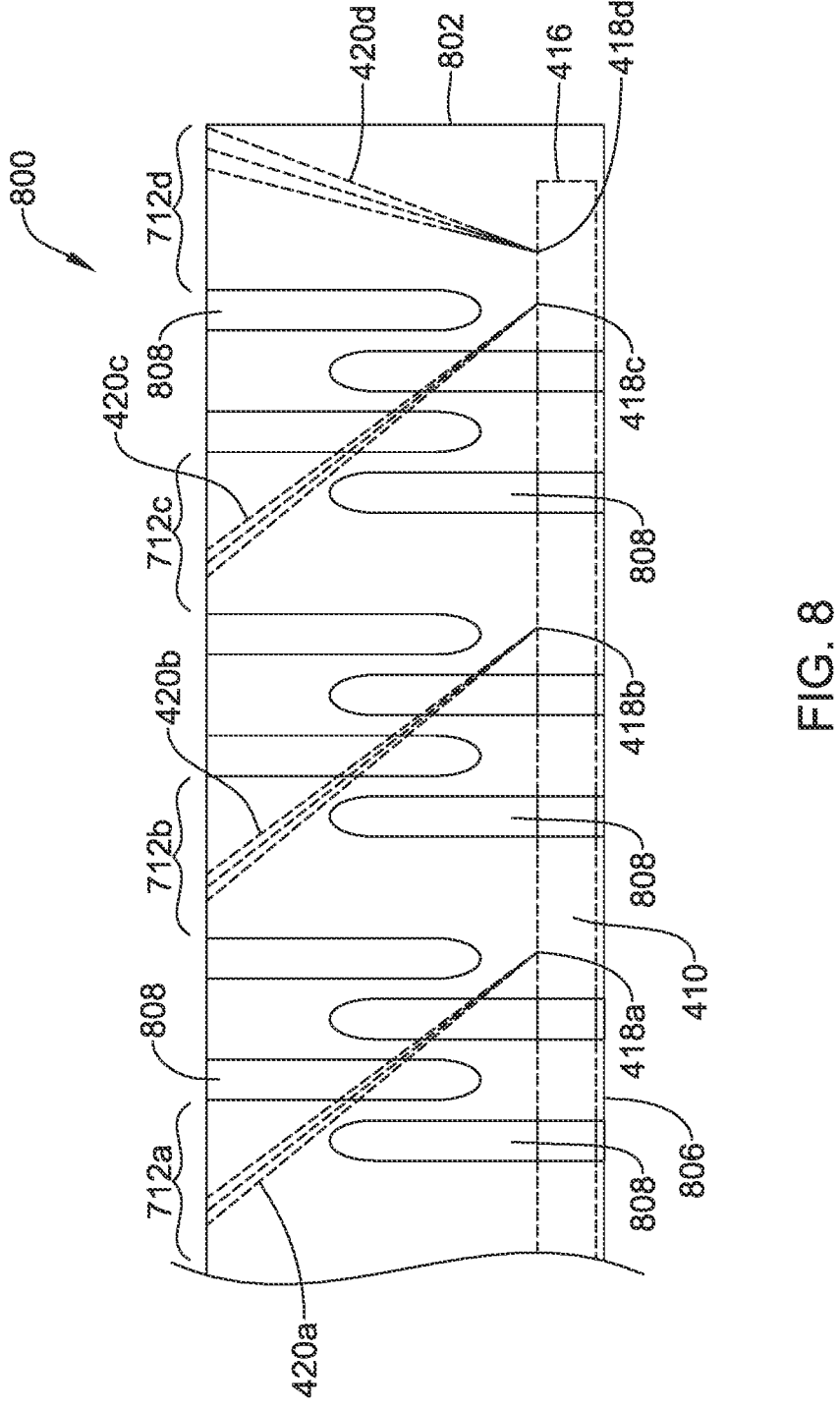
FIG. 8 is a side view of another illustrative reinforcement member.

FIG. 8 is a side view of another illustrative reinforcement member 800 with the high-pressure fluid supply tube 410 that may be used to protect the inner diameter (i.e., luminal surface) of the catheter body 402 (not explicitly shown in FIG. 8) at points of high-pressure impingement. A single monolithic reinforcement member 800 may be configured to extend along a length of the thrombectomy catheter 400 such that the high-pressure jetted motive fluid 420 impinges the reinforcement member 800 rather than directly impacting the inner surface of the catheter body 402. In some embodiments, the reinforcement member 800 may be affixed or secured to the catheter body 402 and in other embodiments, the reinforcement member 800 may be affixed or secured to the high-pressure fluid supply tube 410. The reinforcement member 800 may be formed from a high modulus material that has a high resistance to shear, such as, but not limited to, polyimides, polyether-ether-ketone (PEEK), other high-performance plastics, stainless steel, nitinol, other metals, etc. It is contemplated that the material of the reinforcement member 800 may be selected to withstand the high-pressure impingement of the jetted motive fluid 420. In some examples, the reinforcement member 800 may be heat treated to improve flexibility.

The reinforcement member 800 may have a generally tubular body 806 extending from a first, or distal end 802 to a second, or proximal end configured to be adjacent to a proximal end of the catheter body 402 or proximal to a proximal-most jet orifice 418 of the high-pressure fluid supply tube 410. The tubular body 806 may define a lumen 810 extending from the first end 802 to the second end thereof. The outer diameter of the tubular body 806 may be similar to an inner diameter of the catheter body 402. The reinforcement member 800 may include a plurality of slots 808 cut or otherwise formed into the tubular body 806. The plurality of slots 808 may be formed in any suitable manner. For example, in some embodiments, the slots 808 are formed via laser cutting. In other instances, the slots 808 may be formed by saw cutting, abrasion, or any other known cutting or grinding mechanism. The slots 808 can be dimensioned and/or located to provide a desired level of flexibility. In some examples, the slots 808 have a length that extends circumferentially about the tubular body 806. The slots 808 can be circumferentially and/or longitudinally arranged to provide to provide the desired flexibility. In some instances, the slots 808 may extend helically about the tubular body 806. In some examples, more than one slot 808 may be present a similar longitudinal location. In some instances, the slots 808 may be equally spaced along a length of the tubular body 806. In other cases, the slots 808 may be, for example, more closely spaced together near the first end 802 for additional flexibility and more spaced apart near the second end for additional strength, although this is not required. In other cases, the slots 808 may be more closely spaced together near the second end and more spaced apart near the first end 802. In an illustrative but non-limiting embodiment, the slots 808 may have a width that is in the range of about 0.0005 inches (0.0127 millimeters (mm)) to about 0.020 inches (0.508 mm). Each slot 808 may extend about ten percent, about twenty percent, about thirty percent, about forty percent, about fifty percent, about sixty percent, about seventy percent, about eighty percent, about ninety percent or more about the circumference of the tubular body 806.

The tubular body 806 may include a plurality of regions 812*a-d* (collectively, 812) that are free from slots 808 to provide impingement protection for impingement of the high-pressure jetted motive fluid 420 thereagainst. For example, the slots 808 may provide flexibility to the reinforcement member 800 while the generally solid regions 812, which are devoid of the slots, may allow the jetted motive fluid 420 to impact an inner surface of the reinforcement member 800 instead of an inner surface of the catheter body 402. In some examples, slots 808 may be provided in the wall of the tubular body 806 generally opposite from the area of impingement, as shown in FIG. 8. For example, as the jetted motive fluid 420 is not expected to impinge an entire inner circumference of the catheter body 402, the entire circumference of the generally solid regions 812 need not be free from slots 808. However, in some embodiments, an entirety of the circumference of the tubular member 806 adjacent to the generally solid regions 812 may be free from slots 808. The length of the generally solid regions 812 may be determined, at least in part, by an angle of the jet orifices 418 and/or an area of impingement of the jetted motive fluid 420. For example, a jet orifice 418 having an angle closer to 90° may impinge a smaller area of the inner wall of the catheter body 402 than a jet orifice having an angle closer to 0° or 180° relative to a longitudinal axis of the high-pressure fluid supply tube 410. Thus, the closer the angle of the jet orifice 418 is to 90° the smaller (e.g., arc length of the region free from slots and/or length) the generally solid regions 812 of the reinforcement member 800 may be. For example, in the illustrated embodiment, the angle of the distal jet orifice 418*d* is closer to 90° than the proximal jet orifices 418*a-c* and thus the distalmost generally solid region 812*d* may have a length that is less than a length of the more proximal generally solid regions 812*a-c*. However, this is not required. Alternatively, the distalmost generally solid region 812*d* may have a length that is greater that length of the more proximal generally solid regions 812*a-c*. In some examples, the length of each generally solid region 812 may be approximately the same. It is further contemplated that a length of the generally solid region 812 may take into account variability in the jet orifice 418 location and/or bends in the catheter body 402.

In some examples, the generally solid regions or regions that are free from the plurality of slots 808 may be sized, shaped, and/or positioned to protect the catheter body 402 from the impingement locations of both a proximally facing jet orifice 418*c* and a distally facing jet orifice 418*d*. For example, in the illustrated embodiment, the distalmost generally solid region 812*d* of the reinforcement member 800 may be configured to provide impingement protection for a distally oriented jet orifice 418*d* while the more proximal generally solid regions 812*a-c* of the reinforcement member 800 may be configured to provide impingement protection for the proximally oriented jet orifices 418*a-c*. It is contemplated that the reinforcement member 800 may extend distally beyond the distal end 416 of the supply tube wall 412 to provide impingement protection for the distally oriented jet orifice 418*d*. However, this is not required. It is contemplated that the positioning of the plurality of slots 808 may be arranged based on the desired impingement protection desired. Said differently, regions of the tubular body 806 that are free from the plurality of slots 808 may be selected based on the desired impingement protection desired.

In some embodiments, the reinforcement member 800 may be secured to or otherwise incorporated with the catheter body 402 by positioning the reinforcement member 800 on a mandrel and reflowing or otherwise forming the catheter body 402 over the reinforcement member 800. Alternatively, or additionally, the reinforcement member 800 may be secured directly to the high-pressure fluid supply tube 410. For example, the reinforcement member 800 may be welded, glued, adhered, crimped, etc. directly onto the high-pressure fluid supply tube 410 adjacent to the jet orifices 418. The high-pressure fluid supply tube 410 and reinforcement member 800 assembly may then be inserted into the lumen 406 of the catheter body 402.

It is contemplated that during assembly, the reinforcement member 800 may be oriented to provide impingement protection based on the orientation of the jetted orifice 418 and the jetted motive fluid 420. For example, the generally solid regions 812 may be oriented to provide the desired protection depending on the orientation of the adjacent jet orifice 418. In some examples, the generally solid regions 812 may be axially offset from the respective jet orifice 418. In other examples, the reinforcement members 800 may be at an axially similar location as the respective jet orifice 418.

Figure 9:
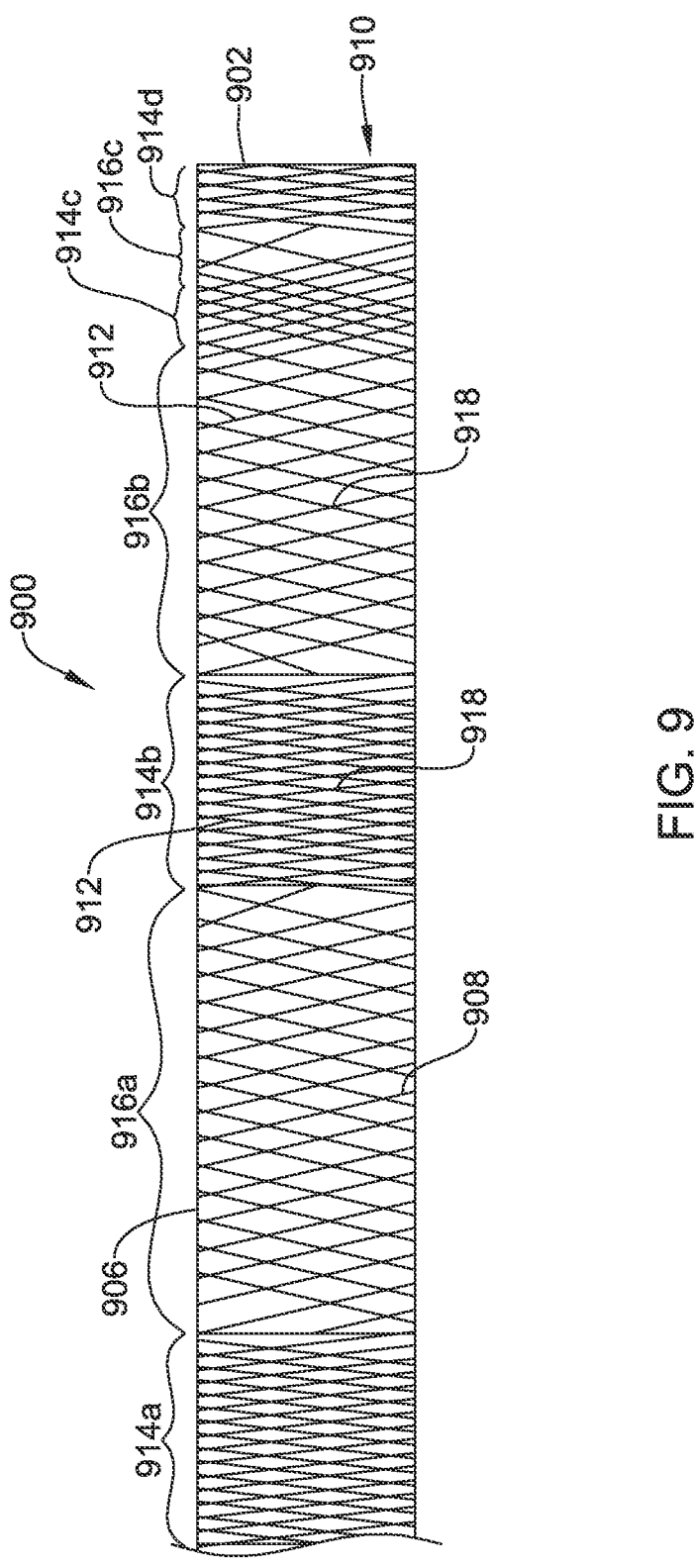
FIG. 9 is a side view of another illustrative reinforcement member.

FIG. 9 is a side view of another illustrative reinforcement member 900 with the high-pressure fluid supply tube 410 that may be used to protect the inner diameter (i.e., luminal surface) of the catheter body 402 (not explicitly shown in FIG. 9) at points of high-pressure impingement. A single length reinforcement member 900 may be configured to extend along a length of the thrombectomy catheter 400 such that the high-pressure jetted motive fluid 420 impinges the reinforcement member 900 rather than directly impacting the inner surface of the catheter body 402. In some embodiments, the reinforcement member 900 may be affixed or secured to the catheter body 402 and in other embodiments, the reinforcement member 900 may be affixed or secured to the high-pressure fluid supply tube 410. In yet other examples, the reinforcement member 900 may be formed as a part of the catheter body 402. The reinforcement member 900 may be formed from a high modulus material that has a high resistance to shear, such as, but not limited to, polyimides, polyether-ether-ketone (PEEK), other high-performance plastics, stainless steel, nitinol, other metals, etc. It is contemplated that the material of the reinforcement member 900 may be selected to withstand the high-pressure impingement of the jetted motive fluid 420. In some examples, the reinforcement member 900 may be heat treated to improve flexibility.

The reinforcement member 900 may have a generally tubular body 906 extending from a first, or distal end 902 to a second, proximal end configured to be adjacent to a proximal end of the catheter body 402 or proximal to a proximal-most jet orifice 418. The tubular body 906 may define a lumen 910 extending from the first end 902 to the second end thereof. The outer diameter of the tubular body 906 may be similar to an inner diameter of the catheter body 402. The tubular body 906 may have a woven structure, fabricated from one or more, or a plurality of filaments or struts 908. In some embodiments, the tubular body 906 may be knitted or braided with a single filament interwoven with itself and defining open cells 912 between adjacent filament segments. In other embodiments, the tubular body 906 may be braided with several filaments interwoven together and define open cells 912 between adjacent filament segments. The filament(s) 908 may each be formed from just one filament or from multiple filaments, as desired. It is further contemplated that the filament 908 may be a wire have a generally circular cross-sectional shape or may be a flat ribbon having a generally rectangular cross-sectional shape. These are just some examples, the filament 908 may take any cross-sectional shape desired. While the tubular body 906 is illustrated has having a generally woven or braided structure, in some cases, the tubular body 906 may be formed from a helically wound filament which forms a helically wound coil, with some longitudinal segments closely wound with no gaps between adjacent windings and other longitudinal segments open wound with gaps between adjacent windings. The closely wound segments may alternate with the open wound segments along the length of the tubular body 906.

The properties of the tubular body 906 may be varied by varying the braid density of the filament(s) 908. For example, the point at which the filament(s) 908 forming the braided structure cross over one another is called a "pic" 918, where "pic" is an acronym for "per inch crossings" and the braid density may be measured in "pics per inch" (PPI). Thus, a higher PPI is associated with a denser braid. The distance between each pic may be referred to as the "pitch" of the braid. Thus, a smaller pitch is associated with a denser braid. It is contemplated that the braid density or tightness may be adjusted by increasing or decreasing the number of pics along the length of the tubular body 906. For example, the PPI of the tubular body 906 may be varied to provide a plurality of regions of impingement protection 914a-d (collectively, 914) and a plurality of more flexible regions 916a-c (collectively, 916). The PPI of the plurality of regions of impingement protection 914 may be greater than the PPI of the more flexible regions 916. In some examples, the pitch of the braid in the regions of impingement protection 914 may be zero or approximately zero such that longitudinally adjacent pics 918 contact each other and the regions of impingement protection 914 are substantially free from open cells 912. In other examples, the pic count of the regions of impingement protection 914 may be in the range of about two times the pic count of the more flexible regions 916. In one illustrative example, for a filament 908 having a width of about 0.003 inches (76.2 micrometers) the flexible regions 916 may have a pic count in the range of 67-77 PPI while the regions of impingement protection 914 may have a pic count in the range of about 135-150. In another example, the flexible regions 916 may have a pic count in the range of about 47-57 PPI and the regions of impingement protection 914 may have a pic count in the range of about 99-109 PPI. These are just some examples. It is contemplated that the regions of impingement protection 914 may have a pic count that is greater than two times the pic count of the flexible regions 916, or may have a pic count that is less than two times the pic count of the flexible regions 916, as desired. It is contemplated that the pic count may be based, at least in part, on a width of the filament 908. For example, a wider filament 908 may provide more coverage that a thinner filament 908 having the same pic count. It is contemplated that the pic count of the regions of impingement protection 914 and/or the pic count of the flexible regions 916 may be selected to provide the desired impingement protection as well as to provide a desired level of flexibility along a length of the reinforcement member 900 based on the width of the filament 908. In yet another example, the pic count may also vary based on the braid or weave pattern of the tubular body 906. It is further contemplated that not all of the regions of impingement protection 914 need have the same pic count. Similarly, not all of the flexible regions 916 need have the same pic count. For example, the flexible regions 916 may progressively become more flexible towards the distal end of the reinforcement member 900 to provide additional flexibility at the distal end 902 and additional strength near the proximal end. This is just one example. In some examples, the flexible regions 916 may be annealed or heat treated to provide additional flexibility, if so desired.

Where the filament 908 is helically wound to form a coil with no cross-over points, the pitch (e.g., distance between adjacent windings) of the filament 908 may be varied in a similar manner. For example, the regions of impingement protection 914 may have a zero pitch (e.g., adjacent windings contact one another) and the flexible regions 916 may have a pitch greater than zero. In some cases, a helically wound coil may be formed from a single filament 908. In other examples, more than one filament 908 may be used for form the helically wound coil. For example, a helically wound coil may be formed from two, three, four, five, or more filaments 908. It is contemplated that the stiffness of the helically wound coil may increase as the number of filaments forming the coil increases. A helically wound coil formed from a single filament 908 may be more flexible than a coil formed from two or more filaments 908 as the wraps of the single filament are more radial whereas the individual filaments of a multiple filament coil may extend more longitudinal than radial, thus increasing the stiffness of the final coil.

It is contemplated that the pic count of the regions of impingement protection 914 may be selected such that the regions of impingement protection 914 are sufficiently dense so as to provide impingement protection. In some embodiments, it may be desirable for the filament(s) 908 in the regions of impingement protection 914 to be as close to one another as possible, or free from open cells 912. For example, this may allow the jetted motive fluid 420 to impact an inner surface of the reinforcement member 900 adjacent the regions of impingement protection 914 instead of an inner surface of the catheter body 402. The length of the regions of impingement protection 914 may be determined, at least in part, by an angle of the jet orifices 418 and/or an area of impingement of the jetted motive fluid 420. For example, a jet orifice 418 having an angle closer to 90° may impinge a smaller area of the inner wall of the catheter body 402 than a jet orifice having an angle closer to 0° or 180° relative to a longitudinal axis of the high-pressure fluid supply tube 410. Thus, the closer the angle of the jet orifice 418 is to 90° the smaller (e.g., shorter) the regions of impingement protection 914 of the reinforcement member 900 may be. It is contemplated that not all of the regions of impingement protection 914 need have the same length. It is further contemplated that in some embodiments, the length of the flexible regions 916 may be greater than the length of the regions of impingement protection 914, although this is not required. The length of the flexible regions 916 may be determined, at least in part, by the distance between the jet orifices 418. It is further contemplated that a length of the regions of impingement protection 914 may take into account variability in the jet orifice 418 location and/or bends in the catheter body 402.

While FIG. 9 illustrates an abrupt or stair-step transition between the regions of impingement protection 914 and the flexible regions 916, this is not required. In some embodiments, a transition region may be positioned between the regions of impingement protection 914 and the flexible regions 916 such that there is a gradual transition between a higher pic count region and a lower pic count region.

In some examples, the regions of impingement protection 914 may be sized, shaped, and/or positioned to protect the catheter body 402 from the impingement locations of both a proximally facing jet orifice 418c and a distally facing jet orifice 418d. It is contemplated that while not explicitly shown, the reinforcement member 900 may extend distally beyond the distal end 416 of the supply tube wall 412 to provide impingement protection for the distally oriented jet orifice 418d. However, this is not required. It is contemplated that the positioning of the regions of impingement protection 914 may be arranged based on the desired impingement protection desired. Said differently, regions of the tubular body 906 that include a higher pic count may be selected based on the desired impingement protection desired.

In some embodiments, the reinforcement member 900 may be secured to the catheter body 402 by positioning the reinforcement member 900 on a mandrel and reflowing or otherwise forming the catheter body 402 over the reinforcement member 900. Thus, the reinforcement member 900 may form the inner surface of the catheter body 402 defining the lumen 406. Alternatively, or additionally, the reinforcement member 900 may be secured directly to the high-pressure fluid supply tube 410. For example, the reinforcement member 900 may be welded, glued, adhered, crimped, etc. directly onto the high-pressure fluid supply tube 410 with the regions of impingement protection 914 adjacent to the jet orifices 418. The high-pressure fluid supply tube 410 and reinforcement member 900 assembly may then be inserted into the lumen 406 of the catheter body 402.

It is contemplated that during assembly, the reinforcement member 900 may be oriented to provide impingement protection based on the orientation of the jetted orifice 418 and the jetted motive fluid 420. For example, the regions of impingement protection 914 may be oriented to provide the desired protection depending on the orientation of the adjacent jet orifice 418. In some examples, the regions of impingement protection 914 may be axially offset from the respective jet orifice 418. In other examples, the regions of impingement protection 914 may be at an axially similar location.

While not explicitly shown, in some cases, the regions of impingement protection 914 may be provided as separate and distinct members, similar in form and function to members 500, 600, 700 described herein. For example, a plurality of high pic count braided members may be provided without the interceding lower pic count flexible regions.

Figure 10:
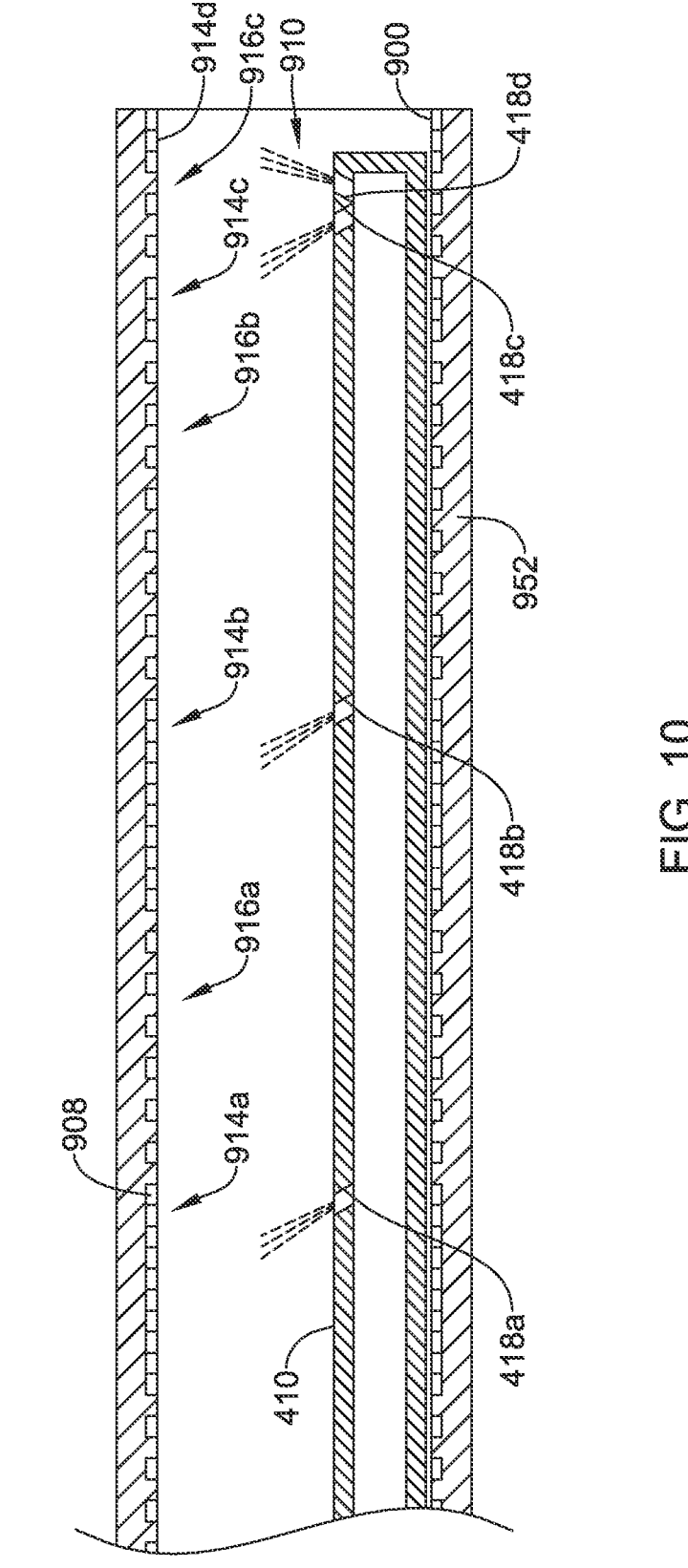
FIG. 10 is a schematic cross-sectional view of an illustrative elongate shaft for use with a thrombectomy catheter.

While in the above assembly method, the reinforcement member 900 is provided in addition to the elongate shaft, in some embodiments, the reinforcement member 900 may replace or be incorporated as a portion of the catheter body 402. FIG. 10 is a schematic cross-sectional view of an illustrative elongate shaft 950 including the reinforcement member 900. The elongate shaft 950 may be similar in form and function to the catheter body 402 described herein. However, the reinforcement member 900 may replace a reinforcement layer (if so provided) of the catheter body 402. For example, the elongate shaft 950 may include the reinforcement member 900 as an inner layer and may further include an outer plastic or polymeric layer 952. This may result in an elongate shaft 950 having a thinner wall than a common three-layer shaft (e.g., an inner polymeric liner, a support member, and an outer layer). Further, a two-layer device may have a larger inner diameter which may increase the performance of the thrombectomy catheter 400. As can be seen, the regions of impingement protection 914 form the at least a portion of the inner surface of the elongate shaft 950 such that the jetted motive fluid 420 impinges the regions of impingement protection 914 as opposed to the outer layer 952. It is further contemplated that reflowing the outer layer 952 over the reinforcement member 900 may allow the outer layer 952 to fill in the open cells 912 of the flexible regions 914. This may provide a smooth, even inner surface of the elongate shaft 950 which may reduce friction and limit turbulence.

The materials that can be used for the various components of the thrombectomy catheter, pump/catheter assembly, and/or other devices disclosed herein may include those commonly associated with medical devices. For simplicity purposes, the following discussion makes reference to the pump/catheter assembly and its related components. However, this is not intended to limit the devices and methods described herein, as the discussion may be applied to other similar devices, tubular members and/or components of tubular members or devices disclosed herein.

The various components of the devices/systems disclosed herein may include a metal, metal alloy, polymer (some examples of which are disclosed herein), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURE-THAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyethere-therketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the pump/catheter assembly and its related components may be doped with, made of, or otherwise include a radiopaque material. Radiopaque materials are understood to be materials capable of producing a relatively bright image on a fluoroscopy screen or another imaging technique during a medical procedure. This relatively bright image aids the user of the pump/catheter assembly and its related components in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the pump/catheter assembly and its related components to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The scope of the disclosure is, of course, defined in the language in which the appended claims are expressed.

What is claimed is:

1. A thrombectomy catheter, comprising:
a catheter body extending from a proximal end region to a distal end region and including an inner surface defining a catheter lumen extending between the proximal end region and the distal end region;
a high-pressure fluid supply tube extending through the catheter lumen from the catheter body proximal end region toward the catheter body distal end region, the high-pressure fluid supply tube configured for communication with a fluid source near the catheter body proximal end region;
at least one jet orifice for expelling at least one fluid jet from said high-pressure fluid supply tube within the catheter lumen;
an entrainment inflow orifice positioned at the distal end region of the catheter body; and
at least one reinforcement member disposed within the catheter lumen;
wherein the at least one fluid jet expelled from the at least one jet orifice is configured to impinge directly against the at least one reinforcement member.

2. The thrombectomy catheter of claim 1, wherein the at least one reinforcement member comprises a generally tubular body including a plurality of slots extending through a sidewall of the generally tubular body.

3. The thrombectomy catheter of claim 2, wherein the plurality of slots each have a length that extends circumferentially about the generally tubular body.

4. The thrombectomy catheter of claim 2, wherein the plurality of slots are longitudinally spaced about a length of the generally tubular body.

5. The thrombectomy catheter of claim 2, wherein the generally tubular body includes at least one region free from the plurality of slots.

6. The thrombectomy catheter of claim 5, wherein the at least one region free from the plurality of slots is positioned adjacent to the at least one jet orifice for impingement of the at least one fluid jet thereagainst.

7. The thrombectomy catheter of claim 1, wherein the at least one reinforcement member comprises a braided tubular body.

8. The thrombectomy catheter of claim 7, wherein the braided tubular body includes regions of a lower pic count alternating with regions of a higher pic count along a length of the braided tubular body.

9. The thrombectomy catheter of claim 1, wherein the at least one reinforcement member comprises a tubular collar and a wing portion extending longitudinally from the collar.

10. The thrombectomy catheter of claim 9, wherein the wing portion is configured to extend less than 270° about an inner circumference of the catheter body.

11. The thrombectomy catheter of claim 1, wherein the at least one reinforcement member is secured to the inner surface of the catheter body.

12. The thrombectomy catheter of claim 1, wherein the at least one reinforcement member is secured to the high-pressure fluid supply tube.

13. The thrombectomy catheter of claim 12, wherein the at least one reinforcement member comprises a plurality of reinforcement members secured to the high-pressure fluid supply tube and axially spaced apart from one another along a length of the high-pressure fluid supply tube.

14. The thrombectomy catheter of claim 1, wherein the at least one reinforcement member comprises polyimide, polyether-ether-ketone (PEEK), stainless steel, or nitinol.

15. The thrombectomy catheter of claim 1, wherein the at least one reinforcement member comprises a generally tubular body secured to the high-pressure fluid supply tube.

16. A thrombectomy catheter, comprising:
a catheter body extending from a proximal end region to a distal end region and including an inner surface defining a catheter lumen extending between the proximal end region and the distal end region;
a high-pressure fluid supply tube extending through the catheter lumen from the catheter body proximal end region toward the catheter body distal end region, the high-pressure fluid supply tube configured for communication with a fluid source near the catheter body proximal end region;
a plurality of jet orifices for expelling a plurality of fluid jets from said high-pressure fluid supply tube within the catheter lumen, the plurality of jet orifices spaced along a length of the high-pressure fluid supply tube;
an entrainment inflow orifice positioned at the distal end region of the catheter body; and
a reinforcement member disposed within the catheter lumen and secured to the inner surface of the catheter body, the reinforcement member comprising a tubular body having an inner surface, wherein the inner surface of the tubular body of the reinforcement member comprises an impingement location for impingement of one of the plurality of fluid jets thereagainst.

17. A thrombectomy catheter, comprising:

a catheter body extending from a proximal end region to a distal end region and including an inner surface defining a catheter lumen extending between the proximal end region and the distal end region;

a high-pressure fluid supply tube extending through the catheter lumen from the catheter body proximal end region toward the catheter body distal end region, the high-pressure fluid supply tube configured for communication with a fluid source near the catheter body proximal end region;

a plurality of jet orifices for expelling a plurality of fluid jets from said high-pressure fluid supply tube within the catheter lumen, the plurality of jet orifices spaced along a length of the high-pressure fluid supply tube;

an entrainment inflow orifice positioned at the distal end region of the catheter body; and a reinforcement member disposed within the catheter lumen, the reinforcement member comprising a generally tubular body having a concave inner surface defining a lumen extending through the tubular body;

wherein the high-pressure fluid supply tube extends through the lumen of the tubular body and is secured to the concave inner surface of the tubular body;

wherein the fluid jet expelled from one of the plurality of jet orifices is configured to impinge directly against the concave inner surface of the tubular body.

18. The thrombectomy catheter of claim 17, wherein the high-pressure fluid supply tube extends along the concave inner surface of the tubular body.

19. The thrombectomy catheter of claim 17, wherein the tubular body is welded to the high-pressure fluid supply tube.

* * * * *